(12) United States Patent
Huo et al.

(10) Patent No.: US 10,233,467 B2
(45) Date of Patent: Mar. 19, 2019

(54) TWO-STAGE PRODUCTION OF HIGHER ALCOHOLS

(71) Applicant: Easel Biotechnologies, LLC, Culver City, CA (US)

(72) Inventors: Yi-Xin Huo, Los Angeles, CA (US); Kwang Myung Cho, Sungnam-Si (KR)

(73) Assignee: Easel Biotechnologies, LLC, Culver City, CA (US)

(*) Notice: Subject to any disclaimer, the term of this patent is extended or adjusted under 35 U.S.C. 154(b) by 0 days.

(21) Appl. No.: 14/422,180

(22) PCT Filed: Aug. 14, 2013

(86) PCT No.: PCT/US2013/054982
§ 371 (c)(1),
(2) Date: Feb. 18, 2015

(87) PCT Pub. No.: WO2014/028642
PCT Pub. Date: Feb. 20, 2014

(65) Prior Publication Data
US 2015/0225750 A1   Aug. 13, 2015

Related U.S. Application Data

(60) Provisional application No. 61/684,669, filed on Aug. 17, 2012.

(51) Int. Cl.
| | | |
|---|---|---|
| C12P 7/64 | (2006.01) | |
| C12P 7/16 | (2006.01) | |
| C12P 7/56 | (2006.01) | |
| C12N 1/00 | (2006.01) | |
| C12N 9/10 | (2006.01) | |
| C12M 1/40 | (2006.01) | |
| C12M 1/00 | (2006.01) | |
| C12P 39/00 | (2006.01) | |
| C12P 13/08 | (2006.01) | |
| C12P 13/06 | (2006.01) | |

(52) U.S. Cl.
CPC .............. *C12P 7/16* (2013.01); *C12M 21/12* (2013.01); *C12M 21/18* (2013.01); *C12M 23/58* (2013.01); *C12P 39/00* (2013.01); *C12Y 101/01001* (2013.01); *C12Y 104/01009* (2013.01); *C12P 7/56* (2013.01); *C12P 13/06* (2013.01); *C12P 13/08* (2013.01); *Y02E 50/10* (2013.01)

(58) Field of Classification Search
CPC .... C12P 7/065; C12P 7/54; C12P 7/16; C12N 1/12
USPC .............................. 435/161, 160, 170, 294.1
See application file for complete search history.

(56) References Cited

U.S. PATENT DOCUMENTS

| | | | |
|---|---|---|---|
| 2010/0105115 A1 | 4/2010 | Simpson et al. | |
| 2010/0317077 A1 | 12/2010 | Gaddy et al. | |
| 2011/0059499 A1* | 3/2011 | Simpson | C12P 7/065 435/161 |
| 2013/0288325 A1* | 10/2013 | Liao | C12N 1/20 435/161 |

FOREIGN PATENT DOCUMENTS

| | | |
|---|---|---|
| WO | 2011-002318 A1 | 1/2011 |
| WO | 2012-061653 A2 | 5/2012 |
| WO | 2012-109534 A2 | 8/2012 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
ISA/KR, International Search Report and Written Opinion, International Appln. No. PCT/US2013/054982, dated Nov. 19, 2013, 13 pages.

* cited by examiner

*Primary Examiner* — Robert B Mondesi
*Assistant Examiner* — Mohammad Y Meah
(74) *Attorney, Agent, or Firm* — Lucas & Mercanti, LLP

(57) ABSTRACT

Methods and systems for the production of alcohols are described. A two stage process is utilized, where fermentation in a first stage produces an intermediate product, such as an amino acid or organic acid, from a carbon containing feedstock. A second stage produces alcohol by fermentation of this intermediate product.

30 Claims, 15 Drawing Sheets

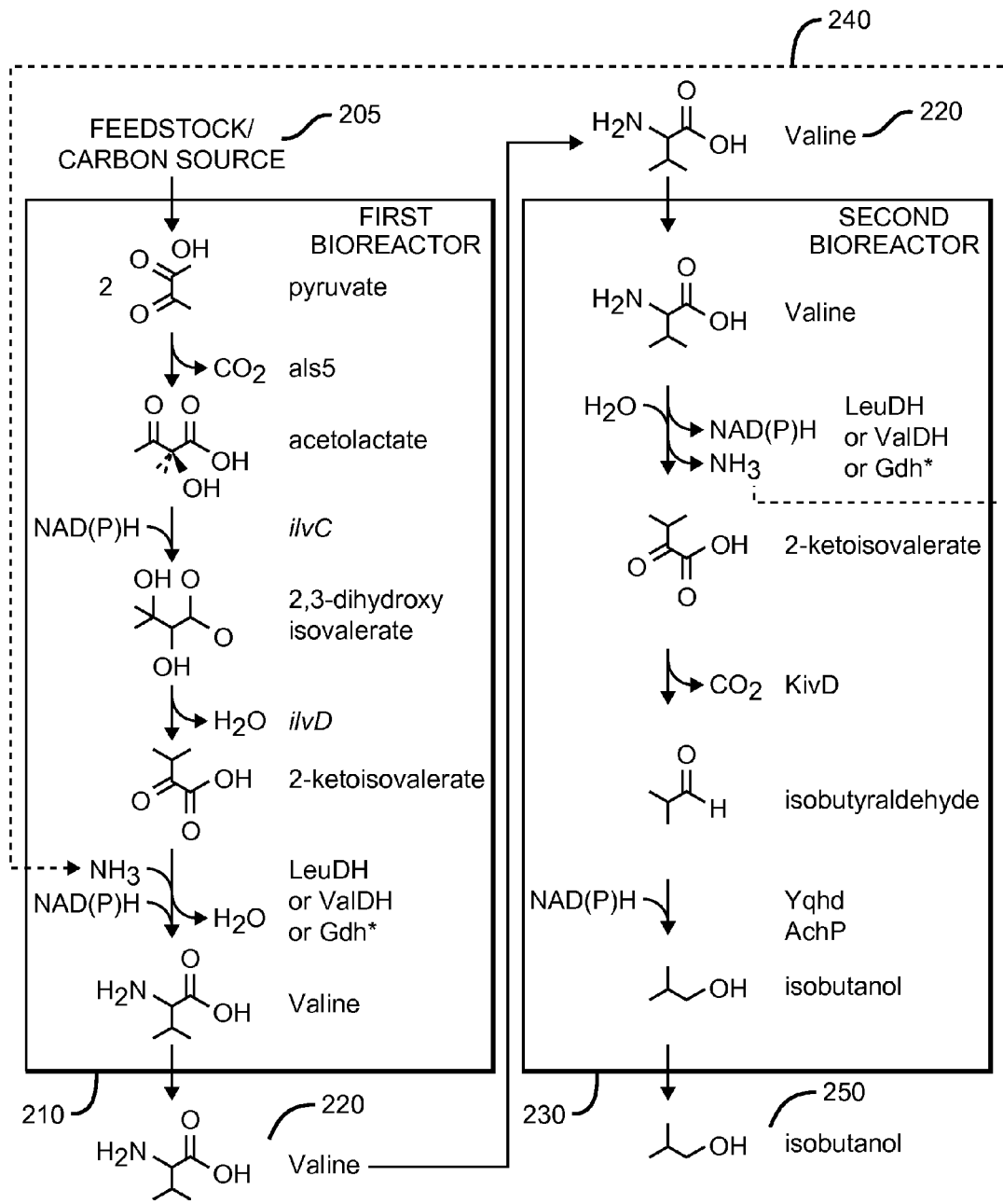
FIG. 2              *Indicates mutant

Note: gdh* means a gdh mutant

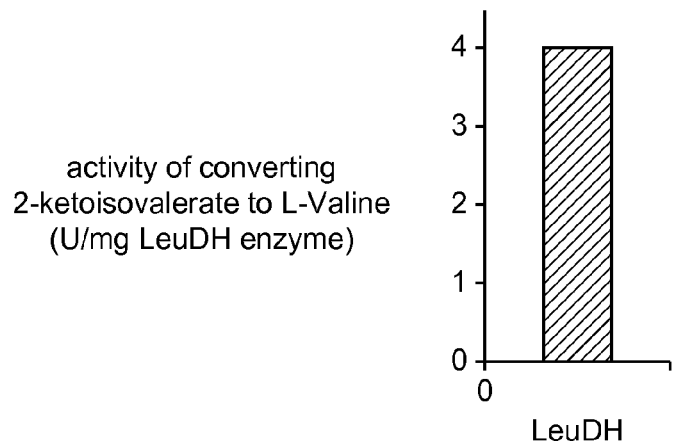
Reaction:
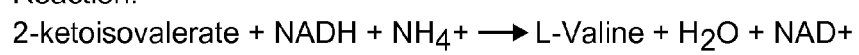
*FIG. 9*
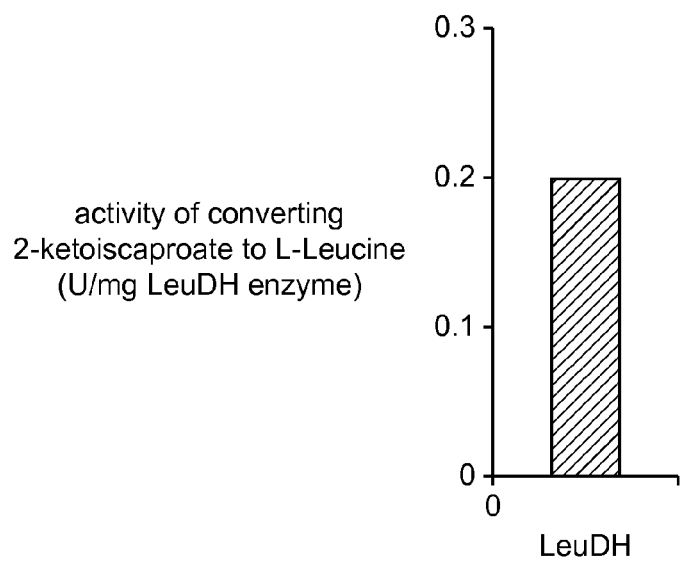
Reaction:
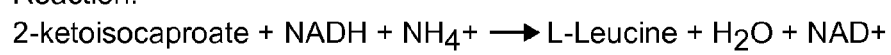
*FIG. 10*

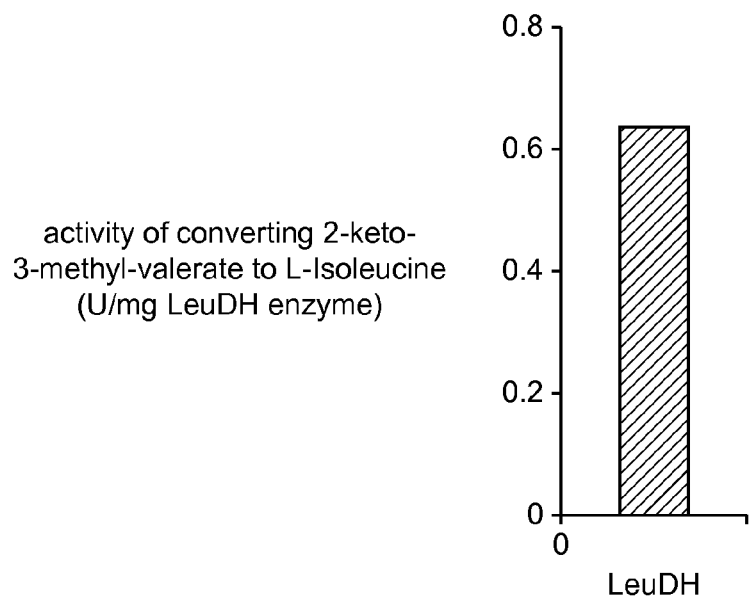
Reaction:
2-keto-3-methyl-valerate + NADH + NH$_4$+ ⟶ L-Isoleucine + H$_2$O + NAD+
*FIG. 11*
*FIG. 12*
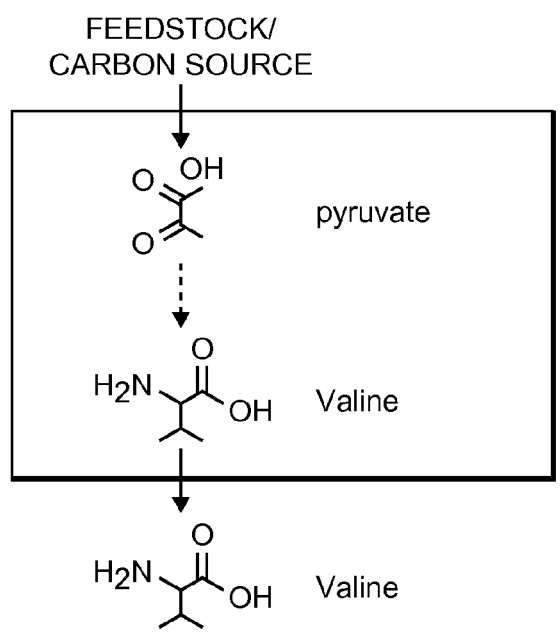

Reaction:
L-Valine + $H_2O$ + $NAD^+$ → 2-ketoisovalerate + NADH + $NH_4^+$

Reaction:
L-Leucine + $H_2O$ + $NAD^+$ → 2-ketoisocaproate + NADH + $NH_4^+$

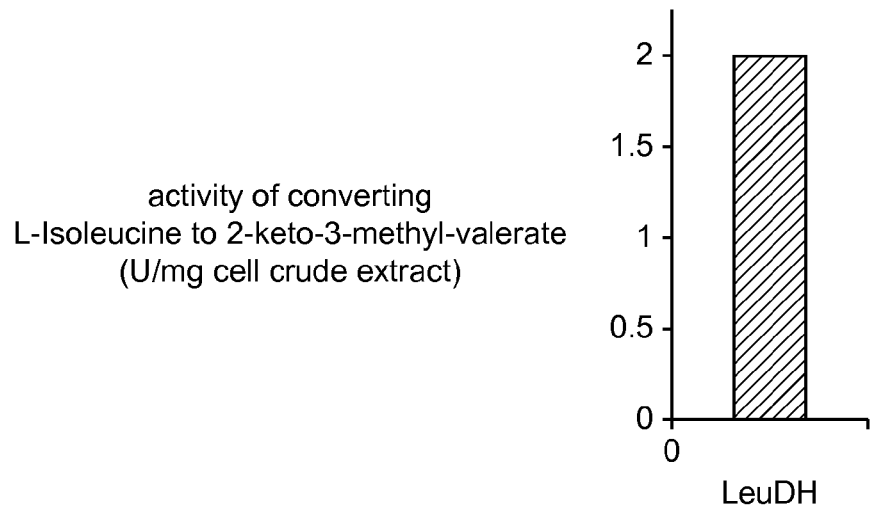
Reaction:
L-Isoleucine + $H_2O$ + $NAD^+$ → 2-keto-3-methyl-valerate + NADH + $NH_4^+$
FIG. 19
FIG. 20
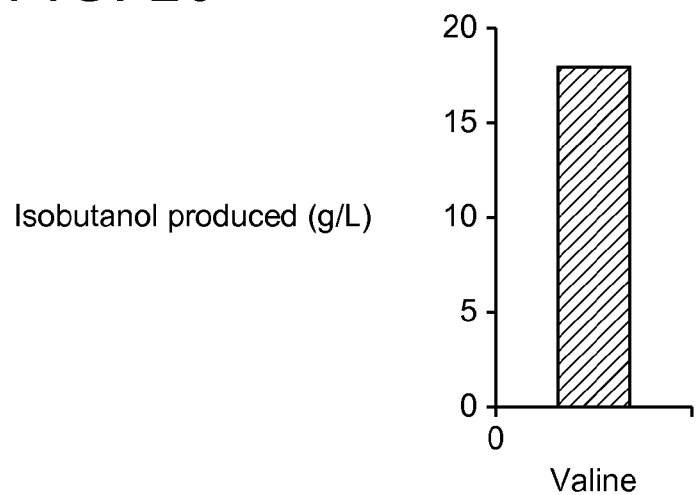
Overall Reaction:
L-Valine + $H_2O$ → Isobutanol + $NH_3$ + $CO_2$

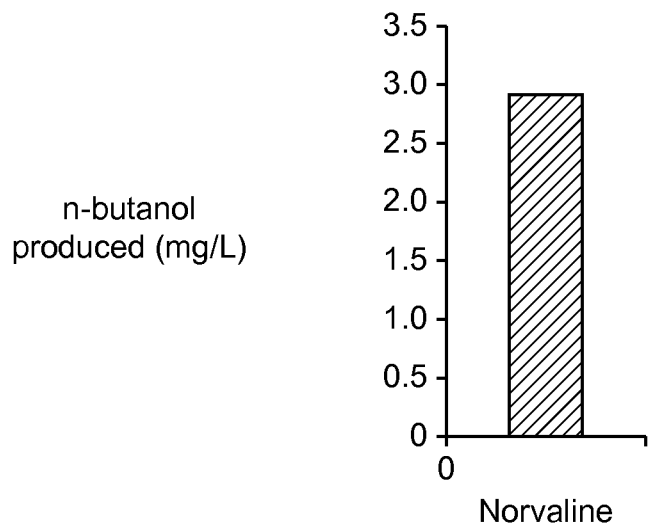
Overall Reaction:
L-Norvaline + $H_2O \rightarrow$ n-butanol + $NH_3$ + $CO_2$
FIG. 21
FIG. 22
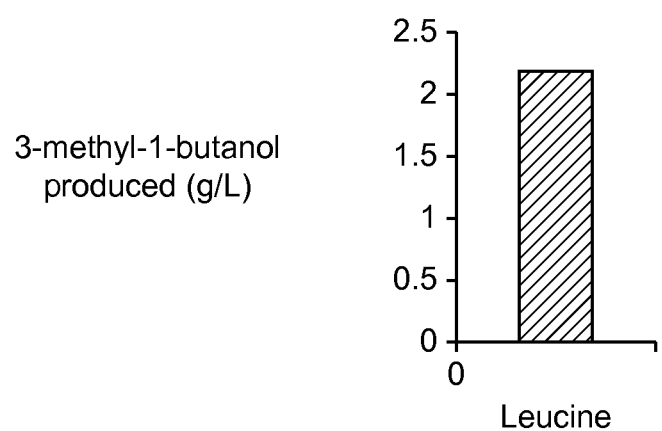
Overall Reaction:
L-Leucine + $H_2O \rightarrow$ 3-methyl-1-butanol + $NH_3$ + $CO_2$

FIG. 23

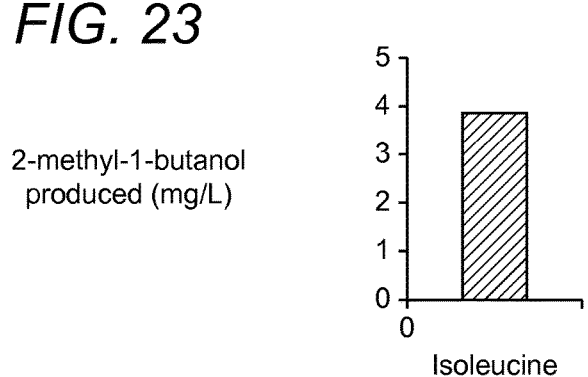

2-methyl-1-butanol produced (mg/L)

Isoleucine

Overall Reaction:
L-Isoleucine + $H_2O$ → 2-methyl-1-butanol + $NH_3$ + $CO_2$

|  | YqhD | AdhA | AdhP |
|---|---|---|---|
| organism | Escherichia coli | Lactococcus lactis | Escherichia coli |
| cofactor | NADPH | NADH | NADH |
| Molecular weight (KD) | 42 | 34 | 35.4 |

B

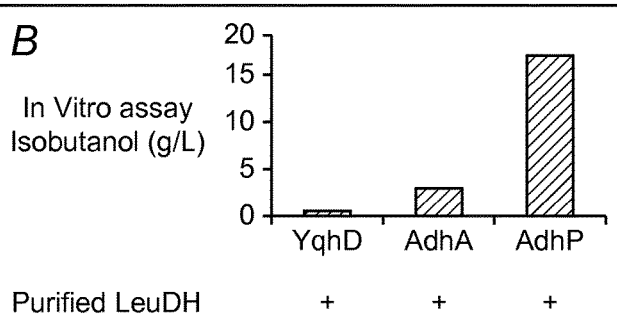

In Vitro assay Isobutanol (g/L)

| | YqhD | AdhA | AdhP |
|---|---|---|---|
| Purified LeuDH | + | + | + |
| Purified KivD | + | + | + |
| Valine | + | + | + |

C

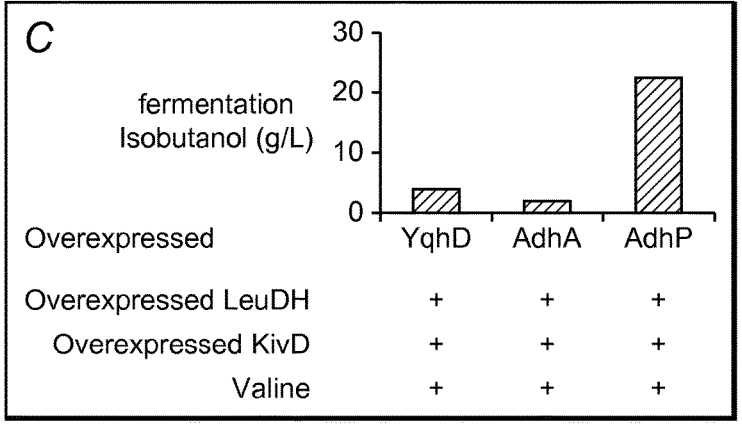

fermentation Isobutanol (g/L)

| | YqhD | AdhA | AdhP |
|---|---|---|---|
| Overexpressed | | | |
| Overexpressed LeuDH | + | + | + |
| Overexpressed KivD | + | + | + |
| Valine | + | + | + |

TWO-STAGE PRODUCTION OF HIGHER ALCOHOLS

This application claims the benefit of priority to U.S. Provisional Application No. 61/684,669, filed Aug. 17, 2012, which is incorporated by reference herein.

FIELD OF THE INVENTION

The invention relates generally to methods and systems for the production of alcohols through fermentative processes, and more specifically, to compositions, methods and systems for the production of higher alcohols, particularly isobutanol, n-butanol, 3-methyl-1-butanol, and 2-methyl-1-butanol.

BACKGROUND

Butanols are an important class of chemicals with utility in a wide range of industrial applications, including use as a solvent and reactive intermediate in organic syntheses, as a solvent in the textile industry, as an extractant in the food industry, and as a slow-evaporating solvent for use in enamels and lacquers. Recently butanols (such as isobutanol) are finding increasing use as an alternative to conventional fossil fuels for use in motor vehicles. Unlike ethanol, such butanol fuels are not corrosive, offer an energy density similar to that of gasoline, and can be used as a direct replacement for petroleum-derived fuels in motor vehicles without the need for extensive engine modifications. Branched chain alcohols, such as isobutanol, 2-methyl-1-butanol, and 3-methyl-1-butanol are particularly attractive in this regard. Currently 10 to 12 billion pounds of butanol are produced annually and needs are projected to increase.

In the United Sates butanols are generally produced by the hydroformylation of propene to form butyraldehyde, which is subsequently reduced to 1-butanol and 2-butanol. Such process, however, relies on nonrenewable resources and result in the release of greenhouse gases to the environment. As a result methods for the production of butanols have been developed that utilize biological processes and renewable starting materials such as biomass.

Butanol production using biological means, also known as biobutanol, is well known. For example, butanol was noted as a byproduct of the A.B.E. process developed by Chaim Weizmann nearly a century ago, in which acetone is produced by fermentation of starch by *Clostridium acetobutylicum*. Production of butanol by this process is low, however. More recently a number of investigators have proposed methods for higher yield production of butanols through the use of genetically modified organisms that ferment simple or crude feedstocks. For example, United States Patent Application No. 2009/0081746 (to J. C. Liao et al.) describes use of a variety of genetically modified organisms with mutations in specific metabolic pathways to ferment sugars and produce a variety of higher alcohol biofuels. Similarly, United States Patent Application No. 2009/0288337 (to S. Picatoggio et al.) discloses the use of genetically modified organisms, such as yeasts, to produce methylbutanol biofuel from amino acid precursors. Such approaches, however, necessarily suffer from relatively low yields that limit their use in large scale operations. Such low yields can be due to metabolic bottlenecks inherent in the enzymatic pathways used. For example, in United States Patent Application No. 2008/261230 (to D-I. Liao, M. J. Nelson, and M. G. Bramucci) it was noted that enzymes in these metabolic pathways may be engineered for high expression in a genetically modified organism, but still remain bottlenecks in a fermentative process due to inherent low specific activity for the production of isobutanol. Since isobutanol and similar compounds are relatively toxic it is not clear if enzymes are or will be available with specific activities high enough to support industrial synthesis of butanols at the relatively low concentrations of butanol precursors generated within a living cell. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

In another approach (as disclosed in U.S. Pat. No. 8,293,509, to S. D. Simpson et al.), a first bioreactor can be used to produce useful alcohols from a crude feedstock and to produce a side product that can be used to enhance the production of butanol from a second, distinct feedstock (such as a carbohydrate) within a second bioreactor. In all of these approaches, however, the inherent toxicity of higher alcohols such as butanol and isobutanol can limit their final concentration in a conventional fermentation process via growth inhibition, metabolic inhibition, and/or death of the productive cells.

Attempts have been made to address the problem of product toxicity in the biological production of butanols. For example, U.S. Pat. No. 8,283,144 (to G. K. Donaldson et al.) describes the use of organisms with resistance (i.e. $IC_{50}$>0.5% w/v) to isobutanol to produce this product by fermentation of sugars. Similarly, United States Patent Application No. 2007/259411 (to M. G. Bramucci et al) discloses a method for improving the resistance of butanol-producing *Enterococcus* strains evolutionary means and their subsequent use in the synthesis of butanol and isobutanol. It is not clear, however, if the concentration of these higher alcohols that can be tolerated are economically recoverable at large scale. Another approach is suggested in United States Patent Application No. 2008/274526 (to M. G. Bramucci et al.), in which the temperature of the fermentation process is reduced in order to improve tolerance to the isobutanol product. Such a reduction in temperature, however, both reduces the rate of isobutanol production and can increase energy costs.

Yet another approach to reducing the effect of product toxicity is to provide a means for segregating biologically produced butanols from the sensitive cell population. One method, disclosed in United States Patent Application (No. 2011/097773, to M. C. Grady et al.), is to provide a water-immiscible solvent system that extracts 1-butanol, 2-butanol, and isobutanol from fermentation media. Large scale application of this approach is limited, however, by the need to occupy a relatively large portion of the fermenter volume with the on-productive solvent system. An alternative approach is disclosed in European Patent No. 0,047,641B1 (to H. G. Lawford), in which the fermentation process is split into an initial phase where little alcohol (in this instance ethanol) is produced and cells replicate rapidly and a second phase where growth-inhibiting concentrations of alcohol are produced by the culture amassed during the initial phase by changing culture conditions. Such an approach, however, retains the metabolic limitations of performing a complete fermentative process within a single organism.

Thus there remains a need for efficient and scalable biological synthesis of alcohols, and particularly branched chain butanols, from simple feedstocks.

SUMMARY OF THE INVENTION

The inventive subject matter provides apparatus, systems and methods by which one can produce branched chain alcohols from a carbon containing feedstock using a two stage reaction sequence. The first stage, which can take place in a first bioreactor, produces an intermediate product that serves as a secondary feedstock for the second stage, which can take place in a second bioreactor. The intermediate product can be a (e.g., branched chain) amino acid and/or an organic acid. Each stage/bioreactor can contain a biological catalyst system, which can include living cells, permeabilized cells, cell free extracts, and/or enzyme preparations. Each stage/bioreactor can have a different biological catalyst system, and can be individually optimized for the reactions that take place in each stage. The intermediate product can be selected so as to be nontoxic to the biological catalyst system of the first stage/bioreactor, permitting accumulation of high concentrations that are not achievable as an intermediate of a metabolic pathway within a conventional single stage method. Such high concentrations of intermediate product can serve to drive unfavorable reaction kinetics in the second stage. In addition, in some embodiments the first bioreactor is not capable of producing the final alcohol product. As used herein, the term "not capable of producing" a compound with respect to a first system or reactor means that production of that compound in the first system or reactor is less than 10% (and more typically less than 5%) of production of the same compound in a second system or reactor, and in some cases production in the first system or reactor is below detectable limit. In some embodiments of the inventive concept the second stage/bioreactor can produce a nitrogen containing byproduct (for example, ammonia) that can be transferred to the first stage/bioreactor and improve efficiency.

One embodiment of the inventive concept is a method for synthesizing a branched chain alcohol by providing a first bioreactor with a first biological catalyst system and a second bioreactor with a second biological catalyst system. The first bioreactor is configured to produce an intermediate product from a feedstock (for example, a gaseous carbon source). Examples of intermediate products can include a branched chain amino acid and/or an organic acid (for example, lactic acid); in some embodiments the first biological catalyst system cannot produce the final product branched chain alcohol. The second bioreactor converts at least a portion of the intermediate product into a branched chain alcohol in which at least about 50% of the carbon of the branched chain alcohol originates from the feedstock utilized in the first bioreactor. In some embodiments of the inventive concept the alcohol produced can include isobutanol, n-butanol, 2-butanol, and/or 3-butanol. In some embodiments of the inventive concept the biological catalyst systems of the first bioreactor and/or the second bioreactor can include a plurality of cells. Such cells can originate from one or more organism(s) selected from one or more of the genus Clostridium, Zymonomas, Escherichia, Salmonella, Rhodococcus, Pseudomonas, Bacillus, Lactobacillus, Enterococcus, Alcaligenes, Klesiella, Paenibacillus, Arthrobacter, Corynebacterium, Brevibacterium, Pichia, Candida, Hansenula, Synechococcus, Synechocystis, Anabaena, Ralstonia, Lactococcus, and/or Saccharomyces, and can include mutant and/or recombinant cells from these genera. In such embodiments the population of cells in the first bioreactor and population of cells in the second bioreactor can be the same or can be different. In other embodiments of the inventive concept the second biological catalyst system can include at least one enzyme. Such an enzyme can be selected from native, mutant, and/or recombinant forms of one or more of the following: a transaminase, a deaminase, a dehydrogenase, a branched chain amino acid transaminase, an 2-keto-acid decarboxylase, an alcohol dehydrogenase, a lactate dehydrogenase, an alpha-acetolactate synthase, a ketol-acid reductase, a dihydroxyacid dehydratase, a leucine dehydrogenase, a valine dehydrogenase, a glutamate dehydrogenase, an alpha-ketoisovalerate decarboxylase, E.C. number 1.1.1.1, E.C. number 1.1.1.2, E.C. number 1.1.1.86, E.C. number 1.1.1.265, E.C. number 1.4.1.2, E.C. number 1.4.1.3, E.C. number 1.4.1.4, E.C. number 1.4.1.8, E.C. number 1.4.1.9, E.C. number 1.4.1.20, E.C. number 2.2.1.6, E.C. number 4.1.1.72, E.C. number 4.1.1.74, E.C. number 4.2.1.9, E.C. number 4.3.1.1, E.C. number 4.3.1.17, E.C. number 4.3.1.18, E.C. number 4.3.1.19, E.C. number 4.3.1.23, E.C. number 4.3.1.24, and E.C. number 4.3.1.25. Such an enzyme(s) can be in the form of a purified enzyme, partially purified enzyme, and/or a substantially cell free extract. In an alternative embodiment of the inventive concept, the second biological catalyst system can include one or more permeabilized cell(s).

Another embodiment of the inventive concept is a system for synthesizing a branched chain or higher alcohol. The system includes a first bioreactor that is configured to convert a feedstock (for example, a gaseous carbon source) into an intermediate product (for example, a branched chain amino acid and/or lactic acid) and a second bioreactor configured to convert the intermediate product into a branched chain or higher alcohol with at least about 50% of the carbon of the branched chain alcohol originating from the feedstock. In some embodiments the first bioreactor can be incapable of producing the final product branched chain or higher alcohol. The first bioreactor and the second bioreactor are operatively coupled to permit the transfer of at least a portion of the intermediate product from the first bioreactor to the second bioreactor. In some embodiments of the inventive concept the second bioreactor can be configured to produce a nitrogen containing byproduct (for example, ammonia), and the system can be configured to transfer at least a portion of the nitrogen containing byproduct from the second bioreactor to the first bioreactor.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 2 depicts an exemplary two stage process for production of isobutanol utilizing a valine intermediate.

FIG. 9 is a bar graph depicting conversion from 2-ketoisovalerate to L-Valine by *Thermoactinomyces intermedius* LeuDH enzyme using an in vitro enzyme process utilizing broken cells (*E. coli* JCL16/pYX51).

FIG. 10 is a bar graph depicting conversion from 2-ketoisocaproate to L-Leucine by *Thermoactinomyces intermedius* LeuDH enzyme using an in vitro enzyme process utilizing broken cells (*E. coli* JCL16/pYX51).

FIG. 11 is a bar graph depicting conversion from 2-keto-3-methyl-valerate to L-Isoleucine by *Thermoactinomyces intermedius* LeuDH enzyme using an in vitro enzyme process utilizing broken cells (*E. coli* JCL16/pYX51).

FIG. 12 is a schematic representation of direct L-valine production by a native or recombinant strain.

FIG. 19 is a bar graph depicting conversion from L-Isoleucine to 2-keto-3-methyl-valerate by *Thermoactinomyces intermedius* LeuDH enzyme using an in vitro enzyme process utilizing broken cells (*E. coli* JCL16/pYX51).

FIG. 20 is a bar graph depicting conversion from L-valine to isobutanol by purified *Thermoactinomyces intermedius* LeuDH enzyme, *Lactococcus lactis* KivD enzyme, and *Escherichia coli* AdhP enzyme using an in vitro enzyme assay.

FIG. 21 is a bar graph depicting conversion from L-Norvaline to n-butanol by purified *Thermoactinomyces intermedius* LeuDH enzyme, *Lactococcus lactis* KivD enzyme, and *Escherichia coli* AdhP enzyme using an in vitro enzyme assay.

FIG. 22 is a bar graph depicting conversion from L-Leucine to 3-methyl-1-butanol by purified *Thermoactinomyces intermedius* LeuDH enzyme, *Lactococcus lactis* KivD enzyme, and *Escherichia coli* AdhP enzyme using an in vitro enzyme assay.

FIG. 23 is a bar graph depicting conversion from L-Isoleucine to 2-methyl-1-butanol by purified *Thermoactinomyces intermedius* LeuDH enzyme, *Lactococcus lactis* KivD enzyme, and *Escherichia coli* AdhP enzyme using an in vitro enzyme assay.

FIG. 24 shows the effect of different alcohol dehydrogenases on the L-Valine to isobutanol conversion. (A) Characteristics of the alcohol dehydrogenases. (B) The in vitro isobutanol production from L-Valine with purified enzymes. (C) The fermentative isobutanol production from L-Valine in flask with strains overexpressing different alcohol dehydrogenases.

DETAILED DESCRIPTION

Figure 1:
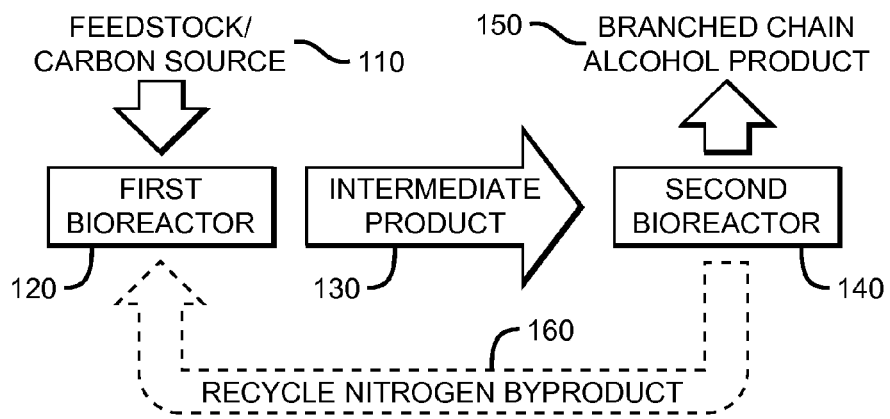
FIG. 1 is a schematic of an embodiment of the inventive concept, depicting a workflow for processing a carbon containing feedstock into a branched chain or higher alcohol using a two stage process.

It should be noted that while the following description is drawn to two stage methods, devices, and systems for producing branched chain alcohols and other desirable products, various alternative configurations are also deemed suitable and may employ various fermentation and/or bioreactor methods and devices, including batch, fed batch, continuous, moving media, packed bed, fibrous bed, bubble reactors, and membrane fermentors, and/or bioreactors, either alone or in combination. Such bioreactors may incorporate organisms, permeabilized cells, substantially cell-free extracts, and/or enzyme preparations that are in solution, in suspension, and/or immobilized.

In preparing the cells and executing the methods of the present invention, it should be understood that standard recombinant DNA and molecular cloning techniques are well known in the art and are described by Ausubel, F. M. et al., *Current Protocols in Molecular Biology*, Greene Publishing Assoc. and Wiley-Interscience, N.Y., 1987. Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994.

One should further appreciate that the disclosed methods and systems provide many advantageous technical effects, including efficient and readily scalable production of various valuable branched chain alcohol products from simple and readily available feedstocks or carbon sources. This is due (at least in part) to the conversion of feedstock to a relatively nontoxic intermediate product in the first stage, which in turn advantageously permits the accumulation of high concentrations of the intermediate product, which when supplied to a second stage can drive enzyme kinetics to produce branched chain alcohols rapidly and efficiently. In addition, the methods and systems disclosed herein can utilize a wide variety of carbon containing feedstocks, including waste gases containing $CO_2$ and CO, thereby producing branched chain alcohols that are highly suitable for use as alternative motor fuels while reducing greenhouse gas emissions.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Branched-chain alcohols can be produced using several different combinations of enzymatic steps, as well as a variety of possible carbon sources. In many currently known productions of branched-chain alcohols such as isobutanol from basic carbon sources (e.g., pyruvate), the production of the corresponding branched-chain amino acid (e.g., valine) is considered to be an undesirable and/or wasteful side product. The inventors, however, have surprisingly found that branched-chain alcohols can be produced with improved productivity, efficiency, and yield when prepared according to methods that include production of such a branched-chain amino acid intermediate, which then serves as starting material in a (preferably physically separated) sequence of biochemical reactions that then produce the branched-chain or higher alcohols.

An exemplary schematic that generally describes one embodiment of the inventive concept is shown in FIG. 1. As depicted, a first stage (first bioreactor 120) and a second stage (second bioreactor 140) are utilized to segregate different portions of the branched chain alcohol production process, with the intermediate being a product of the first stage and a feedstock of the second stage. It should be appreciated that while FIG. 1 illustrates the stages to be physically separated, alternative configurations and methods are also deemed suitable. For example, in some embodiments of the inventive concept the separation is temporal, i.e. the first bioreactor 120 and the second bioreactor 140 occupy the same physical space (or a portion thereof) but are separated by a change in reaction conditions that occurs at a defined point. Examples of suitable reaction condition changes include (but are not limited to) the addition of cells and/or enzymes, removal of cells and or enzymes, the addition of enzyme inhibitors, the addition of one or more cofactors, the addition of a compound that promotes transcription, the addition of a compound that inhibits transcription, a change in temperature, a change in pH, a change in ionic strength, and/or a change in illumination. In other embodiments of the inventive concept a first stage (first bioreactor 120) and second stage (second bioreactor 140) are distinct bioreactors/fermentors. Such a first bioreactor and second bioreactor can be functionally and/or fluidly coupled to each other, for example, to permit transfer of material(s) between them.

As also shown in FIG. 1, in the first stage of a process of the inventive concept a feedstock 110 is supplied to the first bioreactor 120, where it can serve as a carbon source. A wide variety of feedstocks are suitable, including (but not limited to) gaseous carbon sources (for example, gas mixtures containing CO and/or $CO_2$), coal, natural gas, syngas, glycerol, sugars, oligosaccharides, polysaccharides, starch, cellulose, hemicellulose, fatty acids, amino acids, peptides, proteins, whey permeate, cornsteep liquor, sugar beet molasses, barley malt, fermentation waste, sewage, food waste, and/or biomass materials (such as algae, whipgrass, straw, corn stover, sugarcane bagasse, manure, and/or lignocellulosic materials). It should be noted that the feedstock 110 can also include nitrogen-rich material.

First bioreactor 120 processes the feedstock 110 to produce an intermediate product 130 using a first biological catalyst system that can include one or more types of living cells, permeabilized cells, essentially cell-free lysates, and/or enzyme preparations. Enzyme preparations can include purified enzymes (i.e., greater than or equal to 90% pure) and crude enzymes or enzyme preparations (<90% pure). In preferred embodiments of the inventive subject matter, the intermediate product can be a branched chain amino acid, for example valine, leucine, and/or isoleucine. In other preferred embodiments of the inventive subject matter, the intermediate product can also be an organic acid, and most preferably lactic acid. The inventors generally contemplate that the intermediate product can be selected to be a compound and/or compounds that are relatively nontoxic to the first biological catalyst system of the first bioreactor 120, thereby permitting the intermediate product 130 to be accumulated to relatively high concentrations. It should be appreciated that application of a relatively high concentration of intermediate product 130 to the second bioreactor 140 can improve the kinetics of subsequent enzymatic reactions and therefore the overall efficiency of the disclosed processes and methods.

In the second stage of a process of the inventive concept, the intermediate product 130, or a portion thereof, is transferred to a second bioreactor 140. As noted above, this can be accomplished by a physical transfer of the intermediate product 130 between a first bioreactor 120 and a second bioreactor 140, which may or may not include processing of the intermediate product for enrichment or purification from other unwanted substances. A second biological catalyst system within the second bioreactor 140 converts the intermediate product 130 into a branched chain alcohol product 150, such as isobutanol, 3-methyl-1-butanol, and/or 2-methyl-1-butanol. Such a second biological catalyst system can include one or more types of living cells, permeabilized cells, essentially cell-free lysates, and/or enzyme preparations, and can be the same as or different from the first biological catalyst system. Since the branched chain alcohol product 150 is derived from the feedstock 110 a significant portion, if not all, of the carbon of the branched chain alcohol product 150 originates from the feedstock 110. In some embodiments of the inventive concept at least about 50% of the carbon of the branched chain alcohol product 150 originates from the feedstock 110. In other embodiments of the inventive concept at least about 70% of the carbon of the branched chain alcohol product 150 originates from the feedstock 110. In still other embodiments of the inventive concept at least about 90% of the carbon of the branched chain alcohol product 150 originates from the feedstock 110. In other embodiments of the inventive concept essentially all (that is, greater than about 90%) of the carbon of the branched chain alcohol product 150 originates from the feedstock 110.

As still further shown in FIG. 1, in some embodiments of the inventive concept the second bioreactor 140 can also produce a side product 160 that can contain nitrogen, such as ammonia and/or ammonium, and at least a portion of such a nitrogen byproduct 160 can be transferred to the first bioreactor 120. It should be appreciated that such recycling adds greatly to the efficiency of the disclosed methods and processes.

The first biological catalyst system and the second biological catalyst system can be any suitable host cell and can belong to the same species or to different species. For example, they can be independently selected from any appropriate bacterium, archaebacterium, cyanobacterium, filamentous fungus, or yeast. Therefore, the cells can be derived from an organism belonging to any suitable genus such as *Clostridium, Zymonomas, Escherichia, Salmonella, Rhodococcus, Pseudomonas, Bacillus, Lactobacillus, Enterococcus, Alcaligenes, Klesiella, Paenibacillus, Arthrobacter, Corynebacterium, Brevibacterium, Pichia, Candida, Hansenula, Synechococcus, Synechocystis, Anabaena, Ralstonia, Lactococcus* and *Saccharomyces*.

Preferred species include *Escherichia coli, Alcaligenes eutrophus, Bacillus licheniformis, Zymonomas mobilis, Pae-*

*nibacillus macerans, Rhodococcus erythropolis, Pseudomonas putida, Bacillus subtilis, Lactobacillus plantarum, Corynebacterium glutamicum, Enterococcus faecium, Enterococcus gallinarium,* and *Enterococcus faecalis, Saccharomyces cerevisiae, Synechocystis* sp., *Anabaena* sp., *Ralstonia eutropha, Lactococcus lactis* and *Synechococcus elongatus*. Such cells may be native or may contain mutations and/or genetic modifications. Such mutations and/or genetic modifications can result in overexpression of one or more enzymes relative to a native cell. Similarly, such mutations and/or genetic modifications can result in differences in the specific activity of one or more enzymes relative to a native cell. Alternatively, mutations and/or genetic modifications can lead to reduced (or even abolished) expression and/or specific activity of enzymes involved in unwanted side reactions. In some embodiments of the inventive concept, the first biological catalyst system is an *E. coli* cell, or a *C. glutamicum* cell, and the second biological catalyst system is an *E. coli* cell.

In especially preferred embodiments of the inventive concept, the second biological catalyst system may further comprise a native or heterologous keto-acid decarboxylase and a native or heterologous alcohol dehydrogenase. The keto-acid decarboxylase can be a 2-keto-acid decarboxylase, or any enzyme capable of catalyzing the conversion of the keto-acid to its corresponding aldehyde. In some embodiments, the keto-acid decarboxylase has an E.C. number of 4.1.1.72. Suitable genes encoding exemplary keto-acid decarboxylases include *Lactococcus lactis* kivD (GenBank Nos: AAS49166, AY548760; CAG34226, AJ746364, *Salmonella typhimurium* (GenBank Nos: NP-461346, NC-003197), and *Clostridium acetobutylicum* (GenBank Nos: NP-149189, NC-001988). Likewise, the alcohol dehydrogenase can be any suitable enzyme capable of catalyzing the conversion of the appropriate aldehyde to its corresponding alcohol. In some embodiments, the alcohol dehydrogenase has an E.C. number of 1.1.1.1 (alcohol dehydrogenase), 1.1.1.2 (alcohol dehydrogenase (NADP+)) or 1.1.1.265 (3-methyl-butanal reductase). Genes encoding exemplary alcohol dehydrogenases include *S. cerevisiae* (GenBank Nos: NP-010656, NC-001136; NP-014051 NC-001145), *E. coli* (GenBank Nos: NP-417484, NC-000913), and *C. acetobutylicum* (GenBank Nos: NP-349892, NC-003030; NP-349891, NC-003030).

In some preferred embodiments, the first biological catalyst system and the second biological catalyst system are living cells. In other preferred embodiments, the first biological catalyst system is a living cell and the second cell is a permeabilized cell. A permeabilized cell according to the methods of the present invention may include a cell permeabilized by appropriate solvents such as chloroform, hexane, or xylenes, or other useful solvents. In still other embodiments of the inventive concept, the second biological catalyst system can also be an enzyme preparation. Such an enzyme preparation can include one or more native, recombinant, mutant, and/or synthetic enzymes. Suitable enzymes may be supplied as purified enzymes (i.e. greater than or equal to 90% pure), crude enzyme preparations (<90% purity), and/or essentially cell free lysates or extracts. A biological catalyst system or the components thereof can be in form of a solution or flowable suspension. Alternatively, a biological catalyst system or the components thereof can be immobilized, for example to a membrane or insoluble particle.

In especially preferred methods of the present inventive concept, the feedstock (carbon source) is converted to an intermediate product, such as an (e.g., branched-chain or linear) amino acid (for example, valine, norvaline, leucine, isoleucine) or an organic acid (for example, lactic acid), in the first stage of the process by a first biological catalyst system that does not produce the desired branched chain or higher alcohol that is the final product. It is known in the art that branched chain or higher alcohols are relatively toxic; by avoiding production of such compounds in this initial stage the biological catalyst system is not poisoned by the branched-chain or higher alcohol and can exhibit relatively high productivity. At the second stage, a second biological catalyst system can convert the amino acid and/or organic acid to a corresponding branched-chain or higher alcohol (for example, valine to isobutanol) in a biotransformation process. Without being bound by any particular theory, the inventors contemplate that the isobutanol toxicity effect is diminished by separation into two production systems as compared to methods in which isobutanol is produced from a carbon source within a single cell.

In preferred embodiments of the inventive concept, this second stage activity can be decoupled from cell growth, and is internally balanced in terms of reducing equivalents. It should further be noted that this arrangement permits the second stage reaction to proceed at a different rate than the first stage reaction, which is likely to occur when crude or very simple feedstocks/carbon sources are utilized. Segregation of the branched chain alcohol synthesis permits individual optimization of the configuration of and flow rate through the bioreactor associated with each stage. In addition, production of an intermediate product in a separate stage can permit accumulation of such a compound to concentrations far higher than that possible as a metabolic intermediate within a single cell. This accumulation of intermediate product (e.g., branched chain amino acid or an organic acid) permits the application of such a compound to the second stage of the process at high concentrations, which can serve to drive enzymatic processes with unfavorable kinetics at higher rates thereby improving the efficiency and scalability of the disclosed methods and processes.

Some embodiments of the inventive concept can provide a first biological catalyst system, to be used in a step (a) of the methods of the present invention, for example, conversion of a carbon source to a branched chain amino acid. Additionally, the invention can provide a second biological catalyst system, to be used in a step (b) of the methods of the present invention, namely, conversion of the branched-chain amino acid to a branched-chain alcohol. In one aspect of the inventive concept, the invention provides a method for producing branched-chain or higher alcohols, comprising: (a) incubating a first biological catalyst system with a feedstock/carbon source wherein the first biological catalyst system converts the carbon from the feedstock/carbon source to an amino acid; and (b) incubating the amino acid of (a) with a second biological catalyst system, wherein the second biological catalyst system converts the amino acid to a higher alcohol, such that the carbon of the branched chain or higher alcohol is derived primarily from feedstock. In a preferred embodiment of the inventive concept the first biological catalyst system is not capable of producing the branched-chain or higher alcohol of (b).

The produced alcohol is preferably any appropriate higher alcohol, such as isobutanol, n-butanol, 3-methyl-1-butanol, 2-methyl-1-butanol, and combinations thereof. Therefore, suitable branched-chain amino acid intermediates include, for example, valine, leucine, isoleucine, or combinations thereof. In a preferred embodiment, the branched-chain alcohol is isobutanol and the amino acid is valine. In another preferred embodiment, the higher alcohol is n-butanol and the amino acid is norvaline. In another preferred embodiment, the branched-chain alcohol is 3-methyl-1-butanol and the amino acid is leucine. In yet a further preferred embodiment, the branched-chain alcohol is 2-methyl-1-butanol and the amino acid is isoleucine.

Because branched-chain amino acids (valine, leucine and isoleucine) can be produced with low toxicity, in some embodiments of the inventive concept these amino acids can be utilized as substrates for conversion to branched-chain alcohols such as isobutanol, 3-methyl-1-butanol, and 2-methyl-1-butanol, which in turn can be used as biofuels. The two-stage processes exemplarily described herein provide for relatively high-efficiency production of branched-chain amino acids, and subsequent conversion of these amino acids into branched-chain higher alcohols.

Norvaline can be produced by *E. coli* after a down-shift of oxygen (Soini, Jaakko, et al. "Norvaline is accumulated after a down-shift of oxygen in *Escherichia coli* W3110." *Microbial cell factories* 7.1 (2008): 30), in some embodiments of the inventive concept the norvaline can be utilized as substrates for conversion to n-butanol, which in turn can be used as biofuels. The two-stage processes exemplarily described herein provide for the production of norvaline, and subsequent conversion of norvaline into n-butanol.

Existing processes for preparation of such branched-chain amino acids include several steps, typically ending with use of a branched-chain amino acid transaminase (E.C. 2.6.1.42), which converts a keto-acid to a branched-chain amino acid. For example, a typical valine production pathway includes the steps of converting (a) pyruvate to acetolactate; (b) acetolactate to 2,3-dihydroxyisovalerate; (c) 2,3-dihydroxyisovalerate to ketoisovalerate; and (d) ketoisovalerate to valine. In known processes, step (d) is catalyzed by branched-chain amino acid transaminase (EC 2.6.1.42) utilizing glutamate as the nitrogen donor. It is known that glutamate biosynthesis is highly regulated and limits the productivity and yield of the branched-chain amino acid production. The high intracellular glutamate pool in microorganisms is thought to strongly inhibit branched-chain amino acid degradation and the subsequent production of branched-chain higher alcohol in natural processes. As an additional feature of the present invention, it has been surprisingly discovered that ammonium can advantageously be used in place of glutamate as a nitrogen donor by employing a dehydrogenase or deaminase in place of the typical glutamate transaminase. This feature can be employed in both stages of the methods of embodiments of the present invention, i.e., in the final step of branched-chain amino acid synthesis from the feedstock (i.e., converting a keto acid to the corresponding branched-chain amino acid), and also in the first step of branched chain alcohol production from a branched chain amino acid (i.e., converting the branched-chain amino acid to the corresponding keto acid). In some embodiments of the inventive concept the ammonia that is yielded by this process during branched chain alcohol production from branched chain amino acids can be returned for utilization in branched chain amino acid synthesis from a feedstock/carbon source, thereby improving overall process efficiency.

A typical process for conversion of valine to isobutanol by a method of the inventive concept is shown in FIG. 2. For purposes of illustration the two stages of the process are shown as taking place in separate bioreactors, however it should be appreciated that in some embodiments of the inventive concept the exemplary reaction can be performed in a single vessel. As shown in FIG. 2, a feedstock/carbon source 205 is supplied to a first bioreactor 210 that includes a first biological catalyst system. Such a first biological catalyst system can include one or more native cells, one or more native cells expressing mutated or heterologous enzymes, permeabilized cells, a cell free extract, and/or an enzyme preparation. In some embodiments of the inventive concept the first biological catalyst system can be a first cell capable of producing a branched-chain amino acid from a carbon source, but not capable of producing a branched-chain alcohol. In some embodiments, the first cell can be a native cell, i.e., one which has not been modified through mutation and/or recombinant techniques. For example, cells having a deposit number of ATCC 15745 (American Tissue Culture Collection, Manassas, Va.) can be used. In preferred embodiments, the cell comprises one or more heterologous enzymes such as a transaminase, deaminase, or dehydrogenase enzyme, wherein a heterologous enzyme is an enzyme that is derived from an organism other than the one in which the enzyme is produced. In such embodiments, the first cell can comprises one or more of the heterologous deaminase or dehydrogenase enzymes. In some embodiments, the same heterologous transaminase and/or heterologous deaminase and/or heterologous dehydrogenase may be utilized in both stages of the process. In other embodiments of the inventive concept, the first biological catalyst system comprises any combination of native and heterologous enzymes needed to prepare the desired branched-chain amino acid. In the production of valine 220 as an intermediate product, the first biological catalyst system may comprise a native or heterologous acetolactate synthase enzyme, a native or heterologous acetohydroxy acid isomeroreductase, and/or a native or heterologous dihydroxy-acid dehydratase. The acetolactate synthase can be any enzyme capable of catalyzing the conversion of pyruvate to acetolactate. In some embodiments, the acetolactate synthase has an E.C. number of 2.2.1.6. Genes encoding exemplary acetolactate synthases include *Bacillus subtilis* alsS (GenBank Nos: CAB15618, Z99122, NCBI (National Center for Biotechnology Information) amino acid sequence, NCBI nucleotide sequence, respectively), *Klebsiella pneumoniae* (GenBank Nos: AAA25079, M73842), and *Lactococcus lactis* (GenBank Nos: AAA25161, L16975). Likewise, the acetohydroxy acid isomeroreductase can be any enzyme capable of catalyzing the conversion of acetolactate to dihydroxyisovalerate. In some embodiments, the acetohydroxy acid isomeroreductase has an E.C. number of 1.1.1.86. Genes encoding exemplary acetohydroxy acid isomeroreductases include *Escherichia coli* ilvC (GenBank Nos: NP-418222, NC-000913), *Saccharomyces cerevisiae* (GenBank Nos: NP-013459 (SEQ ID NO:181), NC-001144), *Methanococcus maripaludis* (GenBank Nos: CAF30210, BX957220), and *Bacillus subtilis* (GenBank Nos: CAB14789, Z99118). The dihidroxy-acid dehydratase can be any enzyme capable of catalyzing the conversion of dihidroxy isovalerate to ketoisovalerate. In some embodiments, the dihydroxy-acid dehydratase has an E.C. number of 4.2.1.9. Genes encoding exemplary dihydroxy-acid dehydratases include *E. coli* ilvD (GenBank Nos: YP-026248, NC-000913), *S. cerevisiae* (GenBank Nos: NP-012550, NC 001142), *M. maripaludis* (GenBank Nos: CAF29874, BX957219), and *B. subtilis* (GenBank Nos: CAB14105, Z99115). Such enzymes can be supplied as enzyme preparations of any suitable form, including but not limited to highly purified (i.e. greater than or equal to 90% pure) proteins, crude enzyme preparations (i.e. less than 90% pure), and/or essentially cell-free lysates or extracts. In some embodiments of the inventive process the first biological catalyst system can include one or more permeabilized cells. Such permeabilized cells can be produced, for example, by exposure to organic solvents.

As shown in FIG. 2, the valine intermediate product 220 can be transferred from the first bioreactor 210 to a second bioreactor 230 for conversion to isobutanol 250. The second bioreactor 230 includes a second biological catalyst system that is suitable for this purpose. In some embodiments of the inventive concept steps in the conversion of valine to isobutanol include (a) conversion of valine to 2-ketoisovalerate; (b) conversion of 2-ketoisovalerate to isobutyraldehyde; and (c) conversion of isobutyraldehyde to isobutanol. See, e.g., Dickinson et al., *J. Biol. Chem.* 273: 25751-6 (1998). It should be noted that the conversion of ketoisovalerate to valine in the first bioreactor 210 can be catalyzed by a dehydrogenase with the addition of ammonia rather than the branched chain amino acid transaminase (E.C. Number 2.6.1.42) of the prior art, and that the same enzyme can be utilized in the second bioreactor 230 in the conversion of valine to ketoisovalerate with the concomitant loss of ammonia. This permits cycling of ammonia as a nitrogen containing byproduct 240 from the second bioreactor to the first bioreactor, thereby increasing process efficiency. In some embodiments of the inventive concept the second biological catalyst system is a second cell capable of producing a branched-chain alcohol from a branched chain amino acid. In some embodiments, the second cell can be a native cell, i.e., one which has not been modified through mutation or recombinant techniques. In other embodiments, the second cell includes one or more heterologous enzymes. In a preferred embodiment of the inventive concept the second biological catalyst system comprises one or more heterologous enzymes such as a transaminase, a deaminase, and a dehydrogenase. A heterologous enzyme according to the present invention can be any enzyme which does not naturally occur in a host cell. For example, the term can encompass proteins that are encoded by naturally occurring genes found in an organism different from the host cell in which they are produced, or proteins encoded by a mutated or synthetic gene. Any suitable wild-type, mutant, or engineered transaminase, deaminase, or dehydrogenase can be used. In some embodiments, the transaminase has an E.C. number of 2.6.1.42. The deaminase can have an E.C. number such as 4.3.1.1, 4.3.1.17, 4.3.1.18, 4.3.1.19, 4.3.1.23, 4.3.1.24, or 4.3.1.25. Exemplary E.C. numbers for the dehydrogenase include 1.4.1.2, 1.4.1.3, 1.4.1.4, 1.4.1.8, 1.4.1.9. and 1.4.1.20. More specifically, suitable enzymes can include wild type or engineered glutamate dehydrogenase having the EC number 1.4.1.2, 1.4.1.3 or 1.4.1.4; wild type or engineered valine dehydrogenase having the EC number 1.4.1.8; wild type or engineered leucine dehydrogenase having the EC number 1.4.1.9; wild type or engineered phenylalanine dehydrogenase having the EC number 1.4.1.20; wild type or engineered aspartate amino-lyase having the EC number 4.3.1.1; wild type or engineered serine amino-lyase having the EC number 4.3.1.17 or 4.3.1.18; wild type or engineered threonine amino-lyase having the EC number 4.3.1.19; wild type or engineered tyrosine amino-lyase having the EC number 4.3.1.23; wild type or engineered phenylalanine amino-lyase having the EC number 4.3.1.24; or wild type or engineered phenylalanine/tyrosine amino-lyase having the EC number 4.3.1.25. Surprisingly, the inventor has found that the alcohol dehydrogenase/acetaldehyde reductase enzyme that is a product of the adhP gene is particularly useful in the production of branched chain alcohols, such as isobutanol.

Figure 3:
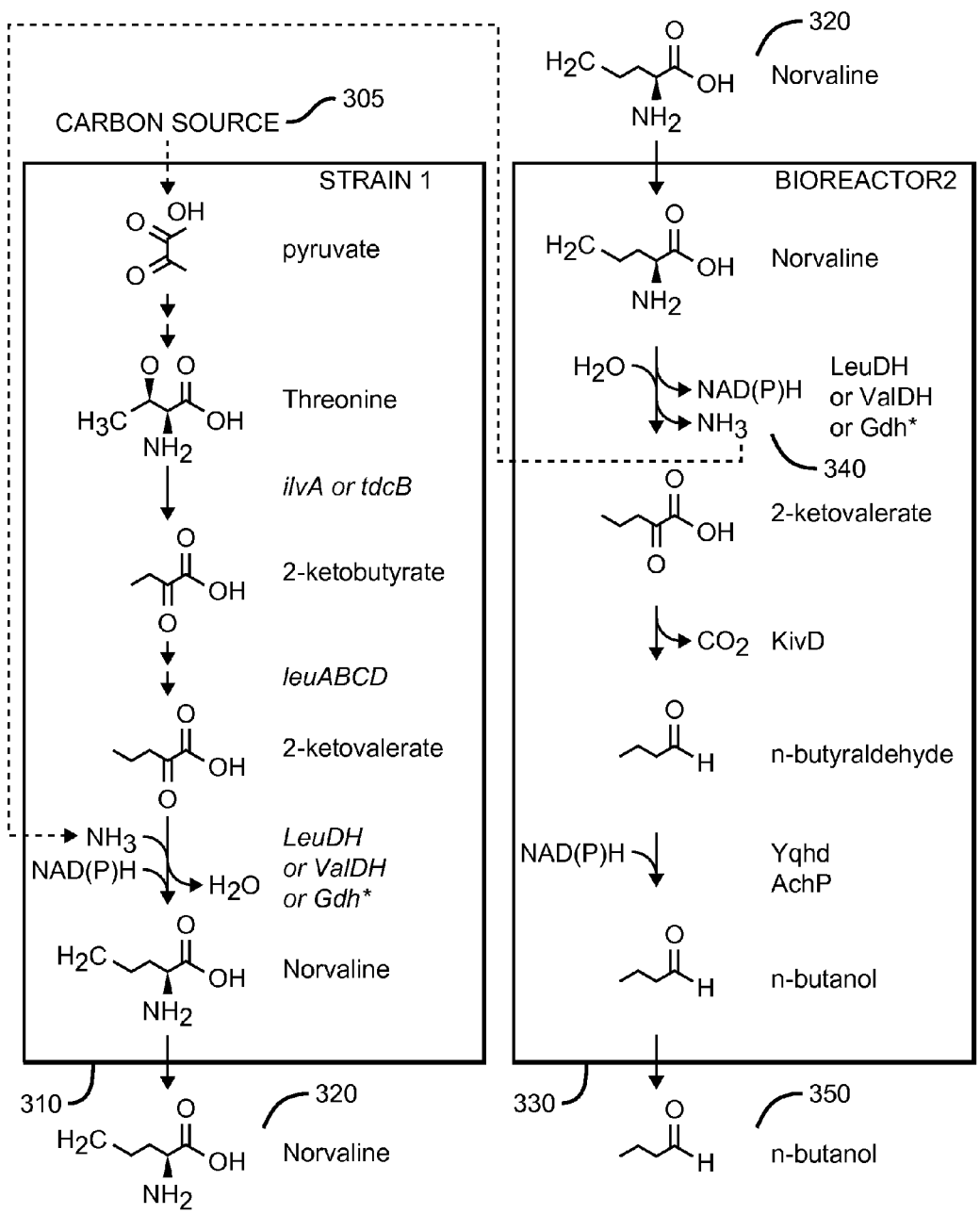
FIG. 3 depicts an exemplary two stage process for production of n-butanol utilizing a norvaline intermediate.

FIG. 3 depicts an exemplary process the inventive concept for the production of n-butanol from a feedstock/carbon source by a two stage method via a norvaline intermediate. As in FIG. 2, a feedstock/carbon source 305 is introduced to a first bioreactor 310 and results in the production of an amino acid intermediate product, in this case norvaline 320. The first bioreactor 310 can include a biological catalyst capable of catalyzing the reactions necessary for the production of norvaline. As described above, the first biological catalyst can include one or more native cells, cells containing mutated or heterologous enzymes, permeabilized cells, a substantially cell free extract, and/or an enzyme preparation. In the conversion of feedstock/carbon source 305 to norvaline 320. With respect to suitable enzymes in the conversion reactions of FIG. 3, the same considerations, enzymes, and preparations as described above for FIG. 2 apply and are not reiterated here. With respect to suitable genes encoding threonine deaminases, all known genes encoding proteins with that enzymatic function are deemed suitable herein, and especially include *Escherichia coli* ilvA (Gene ID: 948287), and/or *Escherichia coli* biodegradative L-threonine dehydrase tdcB (Accession No: EG10990). Likewise, enzymatic conversion of 2-ketobutyrate to 2-ketovalerate can be performed step by step with isopropylmalate synthase (e.g. *Escherichia coli* leuA, Gene ID: 947465), isopropylmalate isomerase (e.g. *Escherichia coli* LeuCD, Gene ID: 945076 and Gene ID: 945642) and isopropylmalate dehydrogenase (e.g. *Escherichia coli* leuB, Gene ID: 944798).

Production of the n-butanol 350 product can be accomplished by transferring at least a portion of the norvaline intermediate product 320 to a second bioreactor 330 that includes a suitable second biological catalyst system. As shown in FIG. 3, such a second biological catalyst system can be similar to that described for production of a branched chain alcohol from a valine intermediate product 220 in FIG. 2. In some embodiments of the inventive concept steps in the conversion of norvaline to n-butanol include (a) conversion of norvaline to 2-keto-valerate; (b) conversion of 2-ketovalerate to n-butyraldehyde; and (c) conversion of n-butyraldehyde to n-butanol. Surprisingly, the inventor has found that the alcohol dehydrogenase/acetaldehyde reductase enzyme that is a product of the adhP gene is particularly useful in the production of higher alcohols, such as n-butanol. It should be noted further efficiencies can be realized by transferring ammonia 340 produced in the second bioreactor 330 to the first bioreactor 310.

Figure 4:
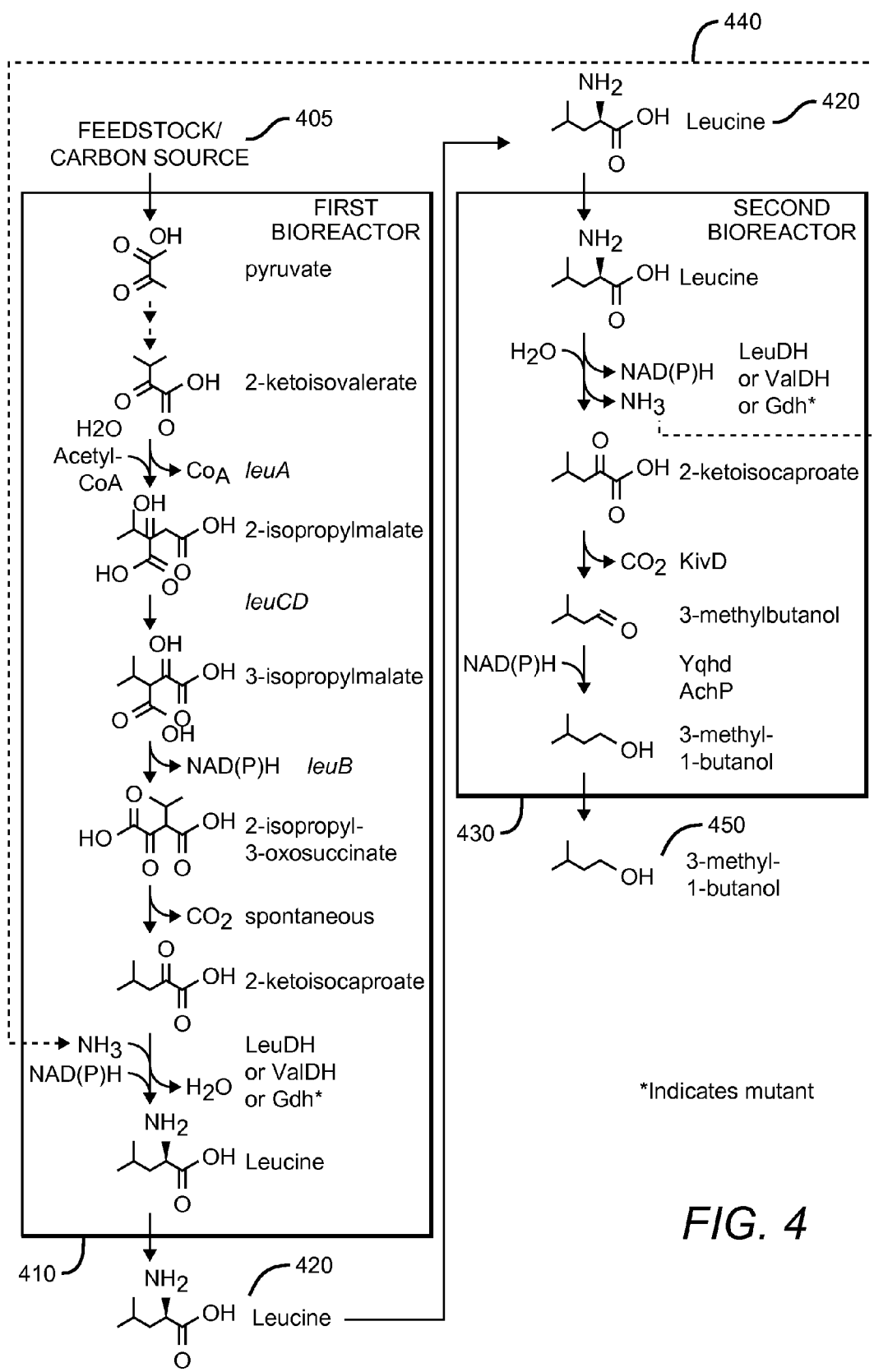
FIG. 4 depicts an exemplary two stage process for production of 3-methyl-1-butanol utilizing a leucine intermediate.

FIG. 4 depicts an exemplary process the inventive concept for the production of 3-methyl-1-butanol from a feedstock/carbon source by a two stage method via a leucine intermediate. As in FIG. 2, a feedstock/carbon source 405 is introduced to a first bioreactor 410 and results in the production of a branched chain amino acid intermediate product, in this case leucine 420. The first bioreactor 410 can include a biological catalyst capable of catalyzing the reactions necessary for the production of leucine. As described above, the first biological catalyst can include one or more native cells, cells containing mutated or heterologous enzymes, permeabilized cells, a substantially cell free extract, and/or an enzyme preparation. In the conversion of feedstock/carbon source 405 to leucine 420, in addition to the enzymes described above for the preparation of valine, the first biological catalyst may further comprise a native or heterologous isopropylmalate synthase, a native or heterologous isopropylmalate isomerase, and/or a native or heterologous isopropylmalate dehydrogenase. The isopropylmalate synthase can be any enzyme capable of catalyzing the conversion of ketoisovalerate to 2-isopropylmalate. In some embodiments of the inventive concept, the isopropylmalate synthase has an E.C. number of 2.3.3.13. Genes encoding exemplary isopropylmalate synthases include *Escherichia coli* leuA (Gene ID: 947465). The isopropylmalate isomerase can be any enzyme capable of catalyzing the conversion of 2-isopropylmalate to 3-isopropylmalate. In some embodiments, the isopropylmalate isomerase has an E.C. number of 4.2.1.33. Genes encoding exemplary isopropylmalate isomerases include *Escherichia coli* leuCD (Gene ID: 945076 and Gene ID: 945642). The isopropylmalate dehydrogenase can be any enzyme capable of catalyzing the conversion of 3-isopropylmalate to 2-isopropyl-3-oxosuccinate. In some embodiments, the isopropylmalate dehydrogenase has an E.C. number of 1.1.1.85. Genes encoding exemplary isopropylmalate dehydrogenases include *Escherichia coli* leuB (Gene ID: 944798).

Production of the 3-methyl-1-butanol 450 product can be accomplished by transferring at least a portion of the leucine intermediate product 420 to a second bioreactor 430 that includes a suitable second biological catalyst system. As shown in FIG. 3, such a second biological catalyst system can be similar to that described for production of a branched chain alcohol from a valine intermediate product 220 in FIG. 2. In some embodiments of the inventive concept steps in the conversion of leucine to 3-methyl-1-butanol include (a) conversion of leucine to 2-keto-isocaproate; (b) conversion of 2-keto-isocaproate to 3-methylbutanal; and (c) conversion of 3-methylbutanal to 3-methyl-1-butanol. Surprisingly, the inventor has found that the alcohol dehydrogenase/acetaldehyde reductase enzyme that is a product of the adhP gene is particularly useful in the production of branched chain alcohols, such as 3-methyl-1-butanol. It should be noted further efficiencies can be realized by transferring ammonia 440 produced in the second bioreactor 430 to the first bioreactor 410.

Figure 5:
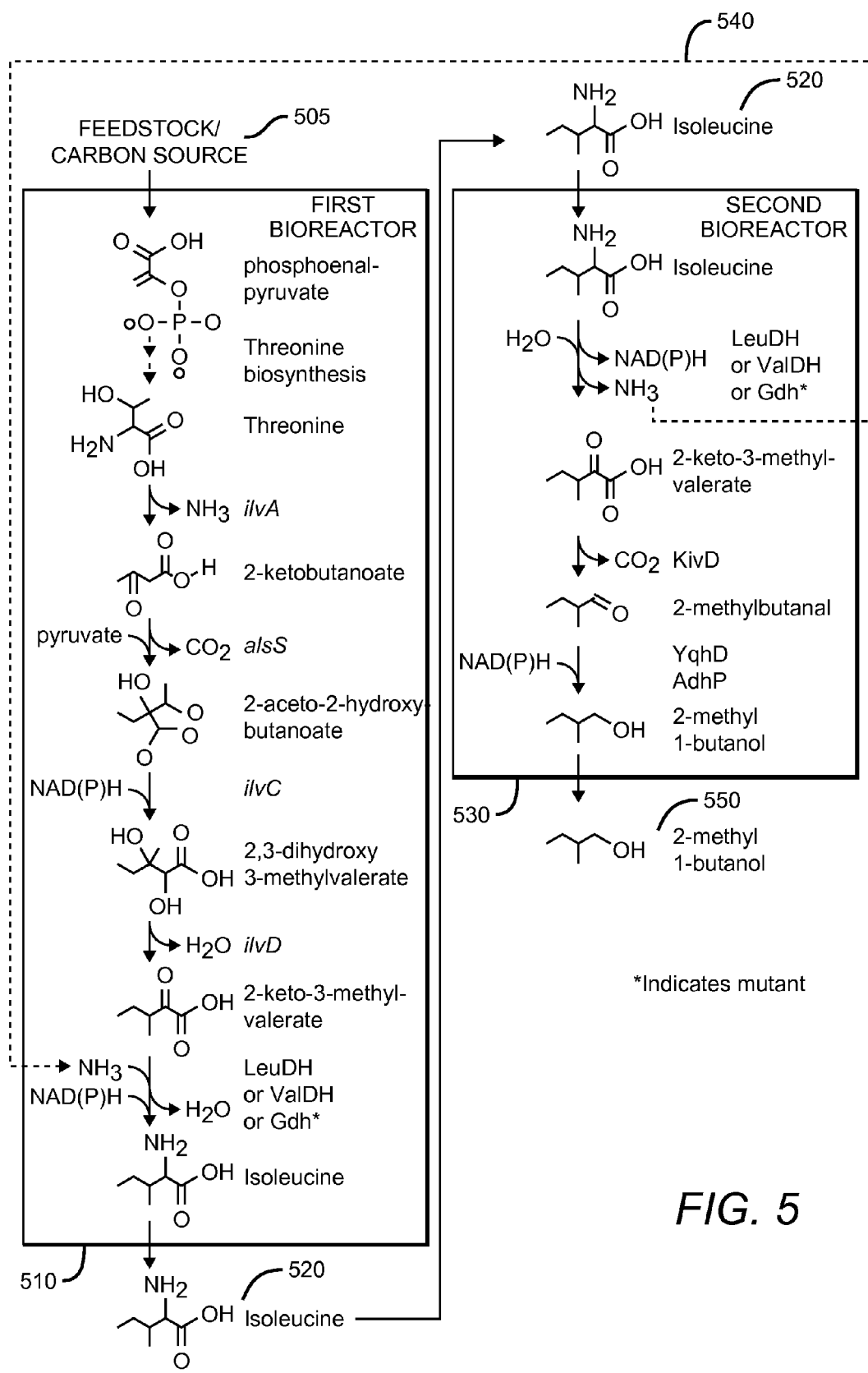
FIG. 5 depicts an exemplary two stage process for production of 2-methyl-1-butanol utilizing an isoleucine intermediate.

A further exemplary embodiment of the inventive concept for the synthesis of 2-methyl-1-butanol via a two stage process utilizing an isoleucine intermediate product is shown in FIG. 5. A feedstock/carbon source 505 is supplied to a first bioreactor 510, which includes a first biological catalyst system. A feedstock/carbon source 505 is introduced to a first bioreactor 510 and results in the production of a branched chain amino acid intermediate product, in this case isoleucine 520. The first bioreactor 510 can include a biological catalyst system capable of catalyzing the reactions necessary for the production of isoleucine 520. As described above, the first biological catalyst system can include one or more native cells, cells containing mutated or heterologous enzymes, permeabilized cells, a substantially cell free extract, and/or an enzyme preparation. In the production of isoleucine 420, the first biological catalyst system can include appropriate native or heterologous enzymes for the synthesis of threonine, which are well known to one of ordinary skill in the art. Additionally, the first biological catalyst system can include a native or heterologous threonine deaminase, which is capable of catalyzing the conversion of threonine to 2-ketobutanoate. In some embodiments of the inventive concept, the threonine deaminase has an E.C. number of 4.3.1.19. Genes encoding exemplary threonine deaminases include *Escherichia coli* ilvA (Gene ID: 948287). The first biological catalyst system can also include a native or heterologous acetolactate synthase as described above, or any enzyme capable of catalyzing the conversion of 2-ketobutanoate to 2-aceto-2-hydroxy-butanoate. The first biological catalyst system can further include a native or heterologous acetohydroxy acid isomeroreductase as described above, or any enzyme capable of catalyzing the conversion of 2-aceto-2-hydroxy-butanoate to 2,3-dihydroxy-3-methylvalerate. The first biological catalyst system can also include a native or heterologous dihidroxy-acid dehydratase as described above, or any enzyme capable of catalyzing the conversion of 2,3-dihydroxy-3-methylvalerate to 2-keto-3-methyl-valerate.

Production of the 2-methyl-1-butanol 550 product can be accomplished by transferring at least a portion of the isoleucine intermediate product 520 to a second bioreactor 530 that includes a suitable second biological catalyst system. As shown in FIG. 4, such a second biological catalyst system can be similar to that described for production of a branched chain alcohol from a valine intermediate product 220 in FIG. 2. In some embodiments of the inventive concept steps in the conversion of isoleucine to 2-methyl-1-butanol include (a) conversion of isoleucine to 2-keto-3-methylvalerate; (b) conversion of 2-keto-3-methylvalerate to 2-methylbutanal; and (c) conversion of 2-methylbutanal to 2-methyl-1-butanol. Surprisingly, the inventors have now discovered that the alcohol dehydrogenase/acetaldehyde reductase enzyme that is a product of the adhP gene is particularly useful in the production of branched chain alcohols, such as 2-methyl-1-butanol. It should be noted that further efficiencies can be realized by transferring ammonia 540 produced in the second bioreactor 530 to the first bioreactor 510.

Other embodiments of the inventive concept can provide a first biological catalyst system, to be used in a step (a) of the methods of the present invention, for example, conversion of a carbon source to an organic acid (for example, lactic acid). Additionally, the invention can provide a second biological catalyst system, to be used in a step (b) of the methods of the present invention, namely, conversion of the organic acid to an alcohol (for example, a branched chain alcohol). In one aspect of the inventive concept, the invention provides a method for producing branched-chain alcohols, comprising: (a) incubating a first biological catalyst system with a feedstock/carbon source wherein the first biological catalyst system converts the carbon from the feedstock/carbon source to an organic acid; and (b) incubating the organic acid of (a) with a second biological catalyst system, wherein the second biological catalyst system converts the organic acid to an alcohol, such that the carbon of the alcohol is derived primarily from feedstock. In a preferred embodiment of the inventive concept the first biological catalyst system is not capable of producing the alcohol of (b). Some embodiments of the inventive concept incorporating the use of an organic acid as an intermediate product in the two stage synthesis of alcohols are shown in FIG. 6 and FIG. 7.

Figure 6:
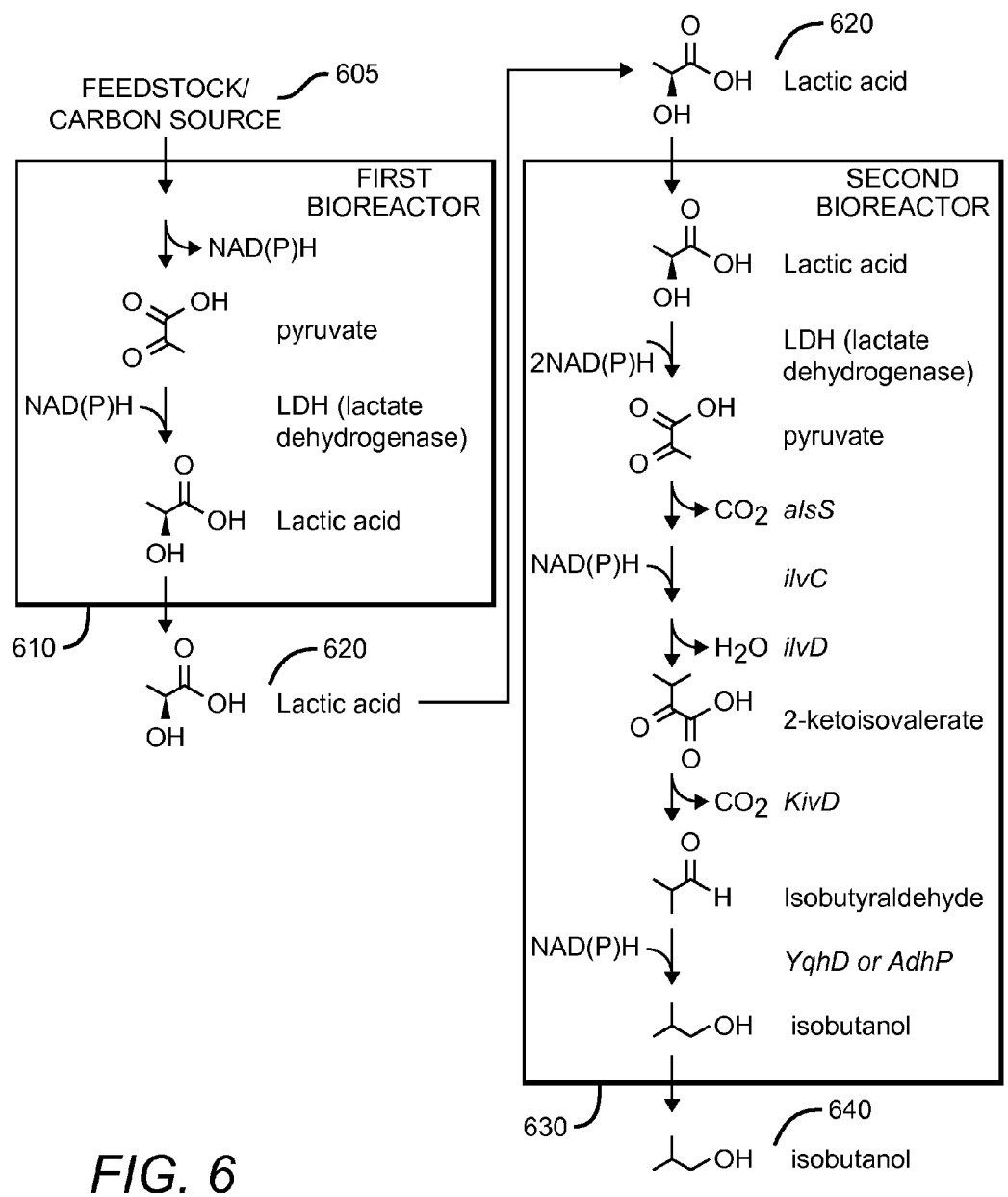
FIG. 6 depicts an exemplary two stage process for production of isobutanol utilizing a lactic acid intermediate.

An embodiment of the inventive concept for the synthesis of isobutanol via a two stage process utilizing a lactic acid intermediate product is shown in FIG. 6. Here, a feedstock/carbon source 605 is supplied to a first bioreactor 610, which includes a first biological catalyst system and results in the production of an organic acid intermediate product, in this case lactic acid 620. The first bioreactor 610 can include a biological catalyst system capable of catalyzing the reactions necessary for the production of lactic acid 620. As described above, the first biological catalyst system can include one or more native cells, cells containing mutated or heterologous enzymes, permeabilized cells, a substantially cell free extract, and/or an enzyme preparation. In the production of lactic acid 620, the first biological catalyst system can include appropriate native or heterologous enzymes for the synthesis of lactic acid. Additionally, the first biological catalyst system can include a native or heterologous lactate dehydrogenase, which is capable of catalyzing the conversion of pyruvate to lactic acid. In some embodiments of the inventive concept, the lactate dehydrogenase has an E.C. number of 1.1.1.27. Genes encoding exemplary lactate dehydrogenases include *Escherichia coli* ldhA (Gene ID: 12930508), *Lactobacillus delbruecki* subspecies *bulgaricus* ldhA (Gene I.D. 4085369), and *Pseudomonas stutzeri* (Gene I.D. 10941313).

Production of the isobutanol 640 product can be accomplished by transferring at least a portion of the lactic acid intermediate product 620 to a second bioreactor 630 that includes a suitable second biological catalyst system. In some embodiments of the inventive concept steps in the conversion of lactic acid to isobutanol include (a) conversion of lactic acid to 2-ketoisovalerate; (b) conversion of 2-ketoisovalerate to isobutyraldehyde; and (c) conversion of isobutyraldehyde to isobutanol. In some embodiments of the inventive concept the second biological catalyst system is a second cell capable of producing a branched-chain alcohol from an organic acid. In some embodiments, the second cell can be a native cell, i.e., one which has not been modified through mutation or recombinant techniques. In other embodiments, the second biological catalyst system includes one or more heterologous enzymes, wherein a heterologous enzyme is an enzyme that is derived from an organism other than the organism that synthesizes the enzyme. For example, the term can encompass proteins that are encoded by naturally occurring genes found in an organism different from the host cell in which they are produced, or proteins encoded by a mutated or synthetic gene. In a preferred embodiment of the inventive concept the second biological catalyst system comprises one or more native or heterologous enzymes such as a synthase, a reductase, a dehydratase, a decarboxylase, and a dehydrogenase. Any suitable wild-type, mutant, or engineered synthase, a reductase, a dehydratase, a decarboxylase, and a dehydrogenase can be used. In some embodiments, the synthase is an acetolactate synthase (E.C. number 2.2.1.6). In other embodiments the reductase is an acetohydroxy acid isomoreductase (E.C. number 1.1.1.86). In still other embodiments the dehydratase is a dihydroxyacid dehydratase (E.C. number 4.2.1.9). In other embodiments of the inventive concept the dehydrogenase is an alcohol dehydrogenase (E.C. number 1.1.1.1). Surprisingly, the inventor has found that the alcohol dehydrogenase/acetaldehyde reductase enzyme that is a product of the adhP gene is particularly useful in the production of branched chain alcohols, such as isobutanol.

Figure 7:
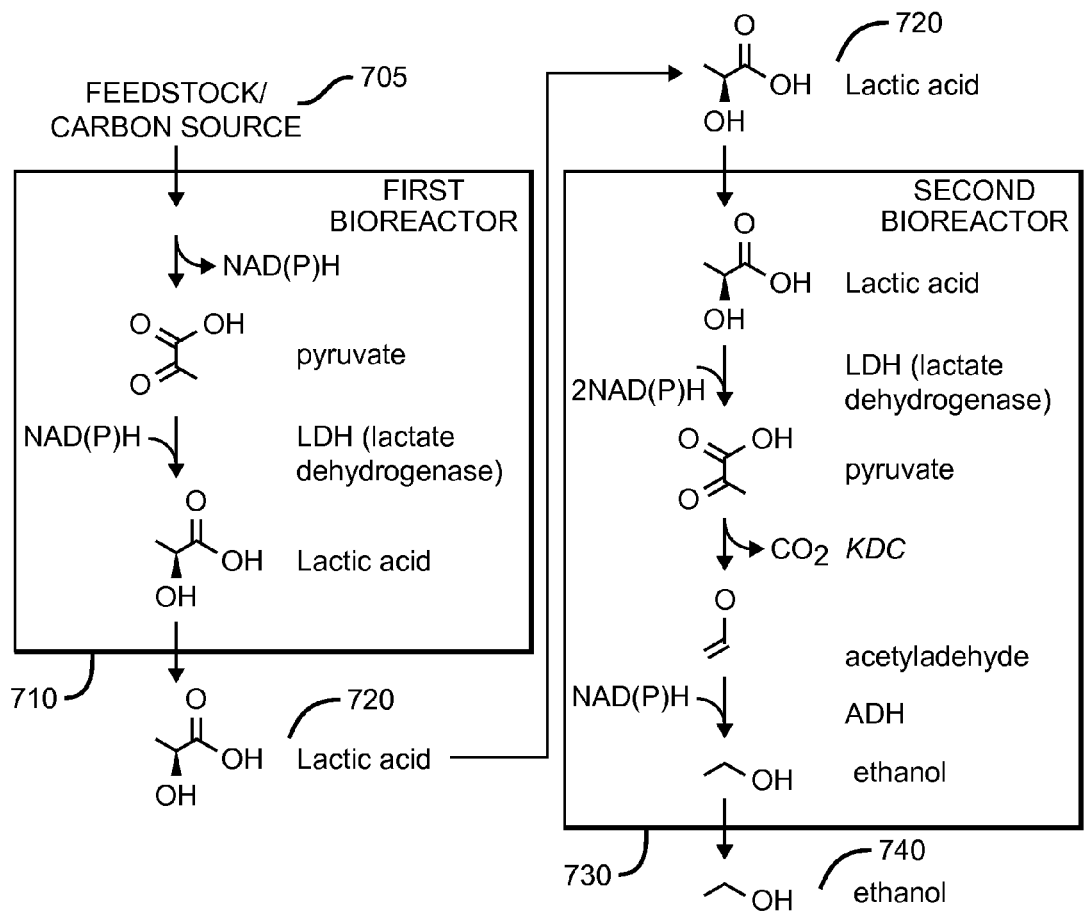
FIG. 7 depicts an exemplary two stage process for production of ethanol utilizing a lactic acid intermediate.

An alternative embodiment of the inventive concept for the synthesis of ethanol via a two stage process utilizing a lactic acid intermediate product is shown in FIG. 7. A feedstock/carbon source 705 is supplied to a first bioreactor 710, which includes a first biological catalyst system and results in the production of an organic acid intermediate product, in this case lactic acid 720. The first bioreactor 710 can include a biological catalyst system capable of catalyzing the reactions necessary for the production of lactic acid 720. As described above, the first biological catalyst system can include one or more native cells, cells containing mutated or heterologous enzymes, permeabilized cells, a substantially cell free extract, and/or an enzyme preparation. In the production of lactic acid 520, the first biological catalyst system can include appropriate native or heterologous enzymes for the synthesis of lactic acid. Additionally, the first biological catalyst system can include a native or heterologous lactate dehydrogenase, which is capable of catalyzing the conversion of pyruvate to lactic acid. In some embodiments of the inventive concept, the lactate dehydrogenase has an E.C. number of 1.1.1.27. Genes encoding exemplary lactate dehydrogenases include *Escherichia coli* ldhA (Gene ID: 12930508), *Lactobacillus delbruecki* subspecies *bulgaricus* ldhA (Gene I.D. 4085369), and *Pseudomonas stutzeri* (Gene I.D. 10941313).

Production of the ethanol 740 product can be accomplished by transferring at least a portion of the lactic acid intermediate product 720 to a second bioreactor 630 that includes a suitable second biological catalyst system. In some embodiments of the inventive concept steps in the conversion of lactic acid to ethanol include (a) conversion of lactic acid to pyruvate; (b) conversion of pyruvate to acetaldehyde; and (c) conversion of acetaldehyde to ethanol. In some embodiments of the inventive concept the second biological catalyst system is a second cell capable of producing an alcohol from an organic acid. In some embodiments, the second cell can be a native cell, i.e., one which has not been modified through mutation or recombinant techniques. In other embodiments, the second biological catalyst system includes one or more heterologous enzymes, wherein a heterologous enzyme is an enzyme that is derived from an organism other than the organism that synthesizes the enzyme. For example, the term can encompass proteins that are encoded by naturally occurring genes found in an organism different from the host cell in which they are produced, or proteins encoded by a mutated or synthetic gene. In a preferred embodiment of the inventive concept the second biological catalyst system comprises one or more native or heterologous enzymes such as a dehydrogenase and/or a decarboxylase. Any suitable wild-type, mutant, or engineered decarboxylase and/or dehydrogenase can be used. In some embodiments, the decarboxylase is a pyruvate decarboxylase (E.C. number 4.1.1.1). In other embodiments the dehydrogenase is a lactate dehydrogenase (E.C. number 1.1.1.24). In still other embodiments the dehydrogenase is an alcohol dehydrogenase (E.C. number 1.1.1.1).

It is also contemplated that in some embodiments of the inventive concept branched chain alcohols (such as, for example isobutanol, 3-methyl-1-butanol, and/or 2-methyl-1-butanol) can be synthesized from feedstock/carbon source using a two stage process that produces alanine as an intermediate product. An example of this process is shown schematically in FIG. 8. A feedstock or carbon source 805 is supplied to a first bioreactor 810, resulting in the production of a valine intermediate product 820. Such a first biological catalyst system can include one or more native cells, one or more native cells expressing mutated or heterologous enzymes, permeabilized cells, a cell free extract, and/or an enzyme preparation. In some embodiments of the inventive concept the first biological catalyst system can be a first cell capable of producing an amino acid from a carbon source, but not capable of producing a branched-chain alcohol. In some embodiments, the first cell can be a native cell, i.e., one which has not been modified through mutation or recombinant techniques. In preferred embodiments, the cell comprises one or more heterologous enzymes such as a transaminase, deaminase, or dehydrogenase enzyme, wherein a heterologous enzyme is an enzyme that is derived from a different organism that that in which the enzyme itself is synthesized. In such embodiments, the first cell can comprises one or more of the heterologous deaminase or dehydrogenase enzymes. In some embodiments, the same heterologous transaminase and/or heterologous deaminase and/or heterologous dehydrogenase may be utilized in both stages of the process. In other embodiments of the inventive concept, the first biological catalyst system comprises any combination of native and heterologous enzymes needed to prepare the desired amino acid.

Figure 8:
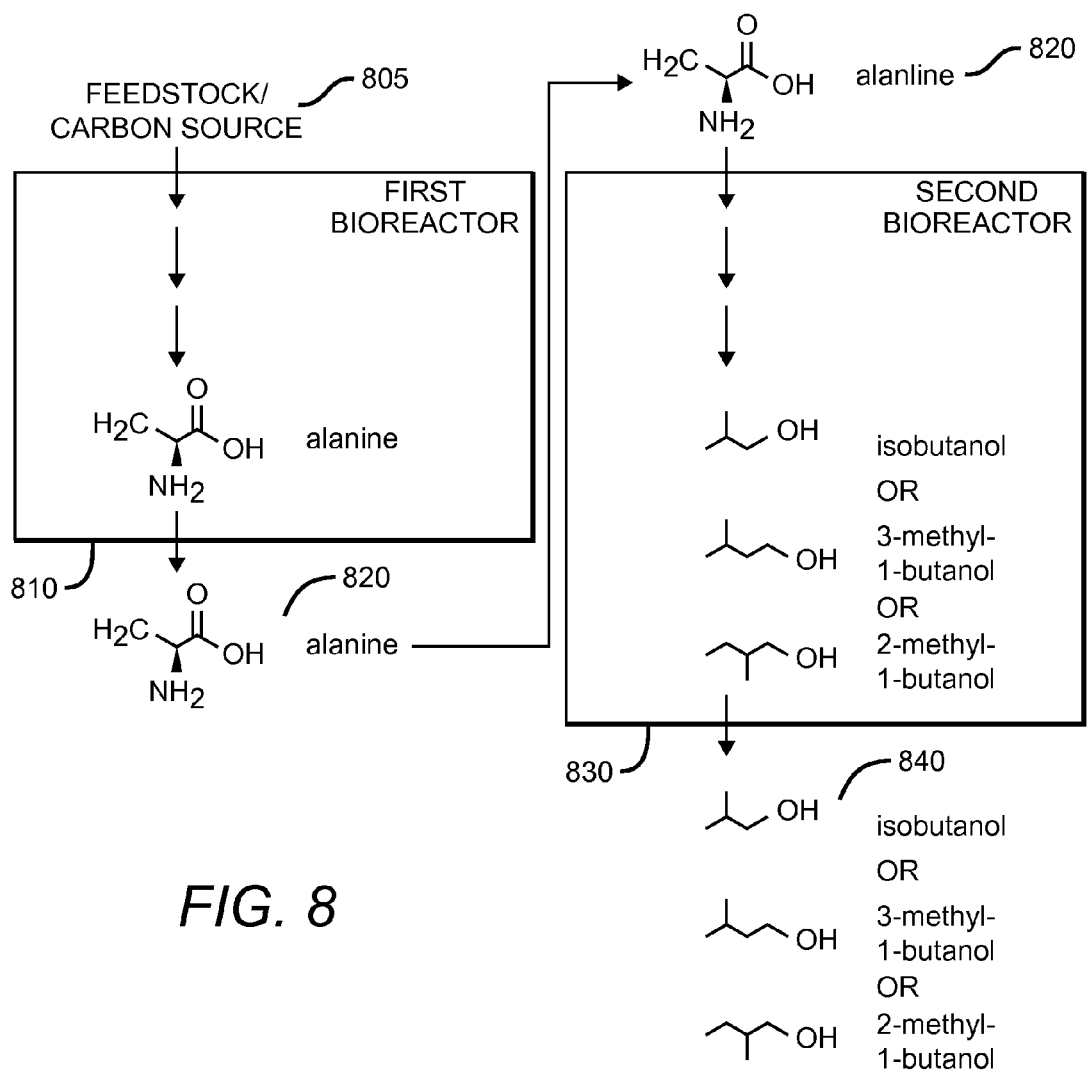
FIG. 8 schematically depicts a general two stage process for production of higher alcohols utilizing alanine as an intermediate.

As shown in FIG. 8, the alanine intermediate product 820 can be transferred from the first bioreactor 810 to a second bioreactor 830 for conversion to a higher alcohol product 250 (such as isobutanol, n-butanol, 3-methyl-1-butanol, and/or 2-methyl-1-butanol). The second bioreactor 830 includes a second biological catalyst system that is suitable for this purpose. In some embodiments of the inventive concept the second biological catalyst system is a second cell capable of producing a branched-chain alcohol from an amino acid. In some embodiments, the second cell can be a native cell, i.e., one which has not been modified through mutation or recombinant techniques. In other embodiments, the second cell includes one or more heterologous enzymes, wherein a heterologous enzyme is an enzyme that is derived from a different organism. In a preferred embodiment of the inventive concept the second biological catalyst system comprises one or more heterologous enzymes such as a transaminase, a deaminase, and/or a dehydrogenase. A heterologous enzyme according to the present invention can be any enzyme which does not naturally occur in a host cell. For example, the term can encompass proteins that are encoded by naturally occurring genes found in an organism different from the host cell in which they are produced, or proteins encoded by a mutated or synthetic gene. Any suitable wild-type, mutant, or engineered transaminase, deaminase, or dehydrogenase can be used.

Exemplary feedstocks/carbon sources, intermediate products, final alcohol products, enzymes utilized in the second stage/bioreactor, and byproducts of methods and systems of the inventive concept are summarized below in Table 1:

TABLE 1

| Feedstock | Carbon Source | | | |
|---|---|---|---|---|
| | Intermediate Product | Final Alcohol Product | Second Stage Bioreactor Enzymes | Second Stage Bioreactor Byproduct |
| Gaseous Carbon (ex: CO, $CO_2$, Syngas) | Valine Norvaline Leucine Isoleucine | Isobutanol n-butanol 3-methyl-1-butanol 2-methyl-1-butanol | LeuDH KivD AdhP | Ammonia |
| Carbohydrate (ex: glucose, xylose, cellulose) | Lactic Acid | Isobutanol | LDH AlsS ilvC ilvD KivD AdhP | |
| Nitrogen Rich Material (ex: amino acid, peptide, protein) | | Ethanol | LDH KDC ADH | |

As noted above, the stages of the alcohol production process are separated or otherwise maintained separately by any suitable manner known to one of ordinary skill in the art. In some embodiments of the inventive concept the stages of a process of the inventive process may be separated temporally (for example, by changing the reaction conditions or composition of the mixture at a given point in time). In an exemplary embodiment, it can be suitable to prepare a fermentation mixture containing the first biological catalyst system and allow that fermentation mixture to progress to a time point where a suitable amount of the desired intermediate product has accumulated. At that time point the second biological catalyst system could be added to or activated within the vessel containing the fermentation mixture.

In other circumstances, it may be desirable to provide a process in which the two biological catalysts are separated in two fermentors, with intermediate product from a first fermentor (or any suitable device) containing the first biological catalyst system transferred to a second fermentor (or any suitable device) for production of the branched chain alcohol product. This arrangement advantageously permits optimization of the configuration of each fermentor. For example, conversion of a single carbon, gaseous carbon source to a suitable intermediate product (such as a branched chain amino acid) may be a slow, high volume process requiring a large bioreactor/fermentor and relatively slow fluid flow rates, whereas production of a branched chain alcohol from the intermediate product may be efficiently carried out by a small, high flow rate bioreactor/fermentor. In some embodiments of the inventive concept the system can be configured so that byproducts from the second bioreactor/fermentor (such as nitrogen containing byproducts) can be transferred to the first bioreactor/fermentor. Transfer of such intermediate products and byproducts can be performed either continuously or incrementally, as is appropriate. For example, such a system may be implemented where the intermediate product (such as a branched-chain amino acid) is continuously or incrementally removed from the first bioreactor/fermentor by a suitable method such as direct pumping of culture broth without separation or partial separation, e.g. by centrifugation or membrane separation (Aharon et al., *Biotech Bioeng*, 41: 287-295 (1993)) of the branch chain amino acid from the first biological catalyst system, and transferred to contact the second bioreactor/fermentor. Alternatively, the first bioreactor/fermentor may be configured to permit essentially complete retention of the first biological catalyst system, for example through immobilization of the first biological catalyst system on a surface (such as for example, a fiber, a particle, or a membrane) or on or within a readily recoverable suspendable media (such as an alginate capsule, a magnetically responsive particle, or a buoyant media). Such retention of the first biological catalyst system advantageously permits essentially continuous production of the intermediate product. The branched-chain alcohol can then be recovered from the second bioreactor/fermentor by any suitable method such as gas stripping, solvent extraction, and/or evaporation and condensation (Baez, A et al., *Appl. Microbiol. Biotechnol*, 90(5):1681-90 (2011).

In some embodiments of the inventive concept a fermentor or bioreactor containing a second biological catalyst system (i.e. one that produces an alcohol) may be configured to receive intermediate products from multiple fermentors or bioreactors containing first biological catalyst systems (i.e. producing intermediate products). For example, a system of the inventive concept can include a primary first stage bioreactor producing a leucine intermediate product and a secondary first stage bioreactor producing an isoleucine intermediate product that are both in fluid communication with a second stage bioreactor producing branched chain alcohols from branched chain amino acids. In such an arrangement either 3-methyl-butanol, 2-methyl-butanol, or a mixture thereof may be produced depending upon which first stage bioreactor (or both) is currently transferring intermediate product to the second stage bioreactor. Alternatively, primary and secondary first stage bioreactors may produce the same intermediate product but be configured to process different feedstocks/carbon sources. For example, a primary first stage bioreactor could be configured utilize $CO_2$ containing flue gases as a feedstock and a secondary first stage bioreactor configured to utilize biomass materials, with both first stage bioreactors configured to produce a valine intermediate product. Either or both of these first stage bioreactors could be coupled to a second stage bioreactor configured to produce isobutanol. Such an arrangement advantageously permits flexibility in plant scheduling and changes in the availability of different feedstocks/carbon sources.

Additionally, one of ordinary skill in the art will understand that in embodiments of the present invention in which direct amination/deamination are used in place of transamination (i.e., deaminases or dehydrogenases in place of transaminases for the conversion of a ketoacid to a branched-chain amino acid as well as the reverse reaction), ammonium can be cycled between the first and second bioreactor/fermentors. That is, ammonium produced through the conversion of the branched-chain amino acid to the branched-chain alcohol may be recovered from the second bioreactor/fermentor and provided to the first bioreactor/fermentor. The transfer of ammonium can be performed using any suitable means, such as gas stripping at high pH. When pH increases, ammonium becomes ammonia which can be separated from water by gas stripping.

In general, one of ordinary skill in the art will understand the various vessels and media which can be used to maintain each type of biological catalyst system, and to separate the products as necessary. It should be further understood that the second biological catalyst system can be endogenously capable of metabolizing carbon sources other than the intermediate product which is provided, however, the second biological catalyst system is in any event capable of converting the intermediate product to a branched-chain alcohol.

The following examples further illustrate the invention but, of course, should not be construed as in any way limiting its scope.

Example 1

This example demonstrates conversion from 2-ketoisovalerate to L-valine by *Thermoactinomyces intermedius* LeuDH enzyme using an in vitro enzyme preparation from broken or permeabilized cells (*E. coli* JCL16/pYX51).

To evaluate the direct deamination activity (i.e., production of branched-chain keto acids from branched-chain amino acids) of *Thermoactinomyces intermedius* LeuDH (E.C. number 1.4.1.9, GenBank ID: CAA55671.1), *E. coli* strain JCL16 was transformed with pYX51. To clone pYX51, primers YXH01 and YXH02 were used to amplify *Thermoactinomyces intermedius* leuDH. The PCR product was digested with Acc65I and SalI and cloned into an empty plasmid pYK digested with the same enzymes.

*E. coli* JCL16 cells with and without pYX51 were grown at 30° C. in 4% yeast extract media for 12 hours following IPTG induction. LeuDH crude extracts were prepared by concentrating the cultures tenfold in 0.1 M phosphate buffer (pH 7.1) and lysing them with 0.1 mm glass beads. Total protein concentrations were measured by Bradford assays. An *E. coli* strain without gene overexpression was used as a background control.

Enzyme activity was determined by mixing 179 mM glycine, 179 mM potassium chloride, 20 mM 2-ketoisovalerate, 10 g/L ammonium chloride, 50 µM β-NADH, and 0.37 mM potassium phosphate with LeuDH crude extracts and incubating at 37° C. Changes in optical density at 340 nm were recorded over time. 1 U was defined as the activity necessary for the formation of 1 µmol NAD+ per min at 37° C. for the reductive amination of 2-ketoisovalerate. Specific activity was expressed as U/mg protein. Typical results are shown in FIG. 9, and show that the LeuDH activity for direct amination for L-valine production is 4.0 U/mg of LeuDH crude extract in this study.

Example 2

This example demonstrates conversion from 2-ketoisocaproate to L-leucine by *Thermoactinomyces intermedius* LeuDH enzyme using an in vitro enzyme preparation from broken or permeabilized cells (*E. coli* JCL16/pYX51).

JCL16 cells were prepared as described in Example 1, with and without pYX51. LeuDH crude extracts were also prepared and analyzed as in Example 1.

Enzyme activity was determined by mixing 179 mM glycine, 179 mM potassium chloride, 20 mM 2-ketoisocaproate, 10 g/L ammonium chloride, 50 µM β-NADH, and 0.37 mM potassium phosphate with LeuDH crude extracts and incubating at 37° C. Changes in optical density at 340 nm were recorded over time. 1 U was defined as the activity necessary for the formation of 1 µmol NAD+ per min at 37° C. for the reductive amination of 2-ketoisocaproate. Specific activity was expressed as U/mg protein. Typical results are shown in FIG. 10, and show that the LeuDH activity for direct amination for L-leucine production is 0.2 U/mg of LeuDH crude extract.

Example 3

This example demonstrates conversion from 2-keto-3-methyl-valerate to L-isoleucine by *Thermoactinomyces intermedius* LeuDH enzyme using an in vitro enzyme preparation from broken or permeabilized cells (*E. coli* JCL16/pYX51).

JCL16 cells were prepared as described in Example 1, with and without pYX51. LeuDH crude extracts were also prepared and analyzed as in Example 1.

Enzyme activity was determined by mixing 179 mM glycine, 179 mM potassium chloride, 20 mM 2-keto-3-methyl-valerate, 10 g/L ammonium chloride, 50 µM β-NADH, and 0.37 mM potassium phosphate with LeuDH crude extracts and incubating at 37° C. Changes in optical density at 340 nm were recorded over time. 1 U was defined as the activity necessary for the formation of 1 µmol NAD+ per min at 37° C. for the reductive amination of 2-keto-3-methyl-valerate. Specific activity was expressed as U/mg protein. Typical results are shown in FIG. 11, and show that the LeuDH activity for direct amination for L-isoleucine production is 0.64 U/mg LeuDH crude extract.

Example 4

This example demonstrates production of L-valine from a suitable carbon source (such as glucose) by an *E. coli* strain that contains ilvBN-ilvC-ilvD-LeuDH genes and that may or may not have the ilvE gene knocked out (FIG. 12).

JCL16 (or, optionally, ΔilvE) cells were transformed as described in Example 1 to contain ilvBN, ilvC, ilvD, and LeuDH genes. In some studies an ilvBN mutant can was used that is resistant to valine feedback inhibition. These cells, as well as non-transformed cells of *E. coli* strain JCL16 were pre-cultured in LB medium with ampicillin (100 µg/mL) at 37° C. overnight on a rotary shaker. Overnight cultures were diluted 1:100 into a different fresh medium. The fresh medium was 1× M9 with 20 g/L glucose and 100 µg/ml ampicillin. 1× modified M9 salt contains 31.5 g/l NaHPO$_4$, 15 g/l KH$_2$PO$_4$, 2.5 g/l NaCl, 1 g/L ammonium chloride, 120 mg/l MgSO$_4$, 11 mg/l CaCl$_2$ and 10 mg/L vitamin B1 per liter water. Cells were then grown 2 hours at 37° C. before adding 0.1 mM isopropyl-β-D-thiogalactoside (IPTG). Fermentation was allowed to proceed for 48 hours.

Alternatively, cells for the production of valine (schematically depicted in FIG. 17) can be prepared using genome-wide random mutagenesis and screening in the presence of an agent such as DL-norvaline for overexpression of L-valine producing mutant strains. Such cells could be provided in a medium using glucose as the sole carbon source and ammonium as the sole nitrogen source. Exemplary general methods of producing suitable *E. coli* mutants can be found in Connor, M. R., Cann, A. F., and Liao, J. C. "3-Methyl-1-butanol production in *Escherichia coli*: random mutagenesis and two-phase fermentation" *Appl Microb. Biotech.* 86 (4): 1155-1164 (2010), which is incorporated herein by reference.

Alcohol compounds produced by the analyzed strains were identified by GC-MS using a model 6890N network GC system, a model 7883B injector and autosampler, and a model 5973 network mass selective detector (Agilent Technologies, Santa Clara, Calif., United States). A DB-5 ms capillary column (30 m, 0.25-mm internal diameter, 0.25-nm film thickness; Agilent Technologies) was used, with helium (1 ml min$^{-1}$) as the carrier gas. Oven temperature was programmed to ramp from 75° C. (2.6 min) to 200° C. at 30° C. min$^{-1}$. The injector and detector were maintained at 250° C. Alcohol compounds were isolated by solvent extraction. Following centrifugation, 300 µL of supernatant of culture broth were extracted with 150 µL GC standard grade toluene (Fluka, St. Louis, Mo., United States). A 1 µL sample was injected in split injection mode with a 30:1 split ratio.

The sample was evaluated for the production of alcohol compounds, as quantified by a model 5890A gas chromatograph and a model 7673A automatic injector, sampler and controller (Hewlett Packard, Palo Alto, Calif., United States) equipped with flame ionization detector. The separation of alcohol compounds is carried out using a DB-FFAP capillary column (30 m, 0.32-mm internal diameter, 0.25-µm film thickness; Agilent Technologies, Santa Clara, Calif., United States). GC oven temperature was initially held at 40° C. for 2 minutes and raised using a gradient of 5° C./min to 45° C. and held for 4 minutes. Temperature was then raised using a gradient 15° C./min until it reached 230° C. and held for 4 minutes. Helium was used as the carrier gas with a 14 p.s.i. inlet pressure. The injector and detector were maintained at 225° C. A 0.5 µL sample was injected in splitless injection mode for characterization, using methanol as an internal standard. Amino acids were quantified using a ZORBAX Eclipse AAA column (Agilent Technologies. Santa Clara, Calif., United States) and an OPA (o-phthaldialdehyde) derivatization method.

No isobutanol was detected in media containing the JCL16 strain or the JCL16 ΔilvE/ilvBN-ilvC-ilvD-LeuDH strain. However, L-valine was produced at measurable levels in media containing the JCL16 ΔilvE/ilvBN-ilvC-ilvD-LeuDH strain. L-valine could not be detected in media containing the JCL16 ΔilvE strain. The resulting L-valine was concentrated and provided to cells in quantities as described in the following Example 5, resulting in the production of isobutanol as generally described in Example 5.

These results show the preparation of cells that can be used to generate L-valine, and that the valine thus produced by such cells can be employed as a starting product for the production of isobutanol.

Example 5

This example demonstrates isobutanol production from L-valine by an *E. coli* strain containing LeuDH-KivD-YqhD genes.

*E. coli* strain JCL16 is a BW25113 (rrnBT14 ΔlacZWJ16 hsdR514 ΔaraBADAH33 ΔrhaBADLD78) derivative with F' transduced from XL-1 blue to supply LacIq. To clone pYX97, three fragments were generated. Plasmid pYX51 was digested with Acc65I and SalI to obtain a fragment containing leuDH. Another plasmid, pYX41, was cloned using primers YX278 and YX279 which were used to amplify *E. coli* yqhD. The PCR product was digested with SphI and cloned into pSA65 digested with the same enzyme. YXH03 and YXH04 were used to amplify kivD and yqhD from pYX41 and the PCR fragment was digested with SalI and BamHI. Plasmid pSA40 was digested with Acc65I and BamHI. The above three fragments were ligated together to create a plasmid. The plasmid was then digested with AatII and SpeI, and the fragment containing leuDH, kivD, yqhD and ColE1 was cloned into pSA55I digested with the same enzymes, creating pYX97. In the presence of isopropyl-β-D-thiogalactoside (IPTG), plasmid pYX97 could overexpress enzymes LeuDH, KivD and YqhD in host *E. coli* strains.

*E. coli* strain JCL16, and the *E. coli* strain JCL16/pYX97 (JCL16 containing the plasmid pYX97) were pre-cultured in test tubes containing LB medium with a ampicillin at 37° C. overnight on a rotary shaker. Overnight cultures were diluted 1:100 into a different fresh medium. The fresh medium was 1× M9 with 10 g/L BD yeast extract and 100 µg/mL ampicillin 1× modified M9 salt contains 31.5 g/l NaHPO$_4$, 15 g/l KH$_2$PO$_4$, 2.5 g/l NaCl, 120 mg/l MgSO$_4$, 11 mg/L CaCl$_2$ and 10 mg/l vitamin B1 per liter water. As analyzed by the provider (Becton Dickinson), 10 g/L BD yeast extract contains 5.41 g/l amino acids, 1.12 g/L ash, 0.76 g/l various salts, 0.31 g/L H$_2$O as well as 1.63 g/l carbohydrate, which is nondegradable by *E. coli*. Cells were then grown for 2 hours at 37° C. before adding 0.1 mM isopropyl-β-D-thiogalactoside (IPTG). After another 2 hours, 2.5 g/L of L-valine were added to specific flasks. Fermentation was performed at 37° C. on a rotary shaker. Fermentation was allowed to proceed for 16 hours.

Alcohol compounds produced by the analyzed strains were identified by GC-MS using a model 6890N network GC system, a model 7883B injector and autosampler, and a model 5973 network mass selective detector (Agilent Technologies, Santa Clara, Calif., United States). A DB-5 ms capillary column (30 m, 0.25-mm internal diameter, 0.25-µm film thickness; Agilent Technologies) was used, with helium (1 ml min$^{-1}$) as the carrier gas. An oven temperature ramp was programmed from 75° C. (2.6 min) to 200° C. at 30° C. min$^{-1}$. The injector and detector were maintained at 250° C. Alcohol compounds were isolated by solvent extraction. Following centrifugation, 300 µL of supernatant from the culture broth was extracted with 150 µL GC standard grade toluene (Fluka, St. Louis, Mo., United States) for analysis of alcohol content. A 1 µL sample was injected in split injection mode with a 30:1 split ratio.

The produced alcohol compounds were quantified using a model 5890A gas chromatograph and a model 7673A automatic injector, sampler and controller (Hewlett Packard Palo Alto, Calif., United States) equipped with flame ionization detector. The separation of alcohol compounds was carried out by A DB-FFAP capillary column (30 m, 0.32-mm internal diameter, 0.25-µm film thickness (Agilent Technologies, Santa Clara, Calif., United States). GC oven temperature was initially held at 40° C. for 2 minutes and raised with a gradient of 5° C. min$^{-1}$ until 45° C. and held for 4 minutes before increasing the temperature at 15° C. min$^{-1}$ until 230° C. was reached and held for 4 minutes. Helium was used as the carrier gas with 14 p.s.i. inlet pressure. The injector and detector were maintained at 225° C. A 0.5-μL sample was injected in splitless injection mode. 1-pentanol was used as the internal standard.

Amino acids were quantified using ZORBAX Eclipse AAA column (Agilent Technologies, Santa Clara, Calif., United States) using an OPA (o-phthaldialdehyde) derivatization method.

Figure 13:
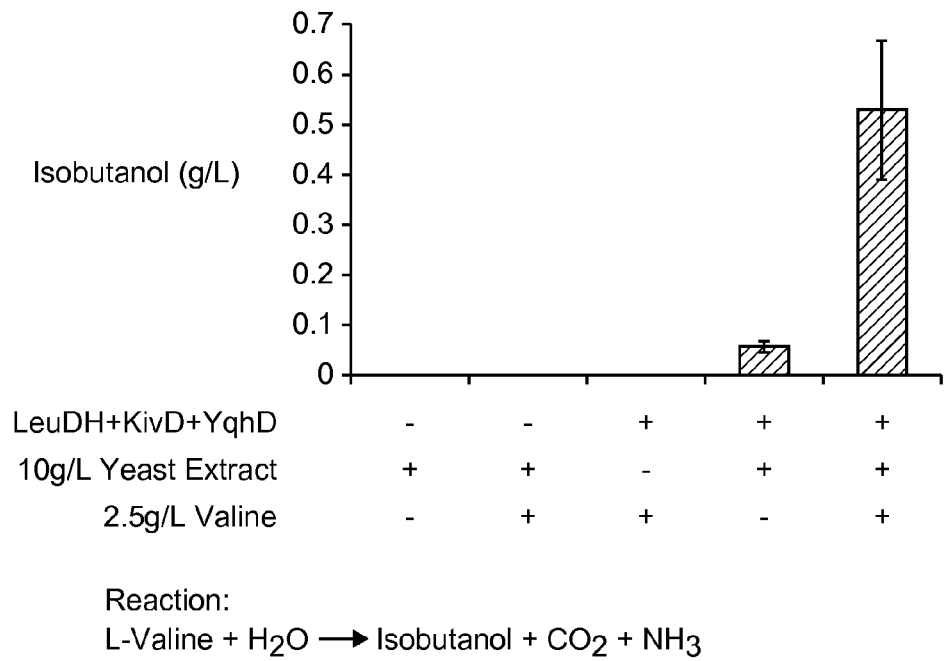
FIG. 13 is a bar graph depicting isobutanol production (g/L) from valine by an *E. coli* strain containing LeuDH-kivD-yqhD genes compared to that of to an *E. coli* strain not containing those genes, in the presence and absence of supplemental valine and yeast extract.

Typical results are shown in FIG. 13. No isobutanol was detected in the broth containing JCL16 strain, regardless of whether or not L-valine had been added. In the absence of valine, low concentrations (0.05 g/L) of isobutanol were detected in the broth containing JCL16/pYX97. In the presence of 2.5 g/L L-valine 0.52 g/L of isobutanol was detected in the broth containing JCL16/pYX97. The theoretical conversion rate from L-valine to isobutanol was 0.63 g/g. These results demonstrate that 0.47 g/L isobutanol was produced directly from 2.5 g/L L-valine by the enzymes LeuDH-KivD-YqhD; approximately 30% of the theoretical yield was achieved in this particular study.

Example 6

This example demonstrates isobutanol production from L-valine by an *E. coli* strain containing LeuDH-KivD-adhP genes.

*E. coli* strain JCL260 is a BW25113 (rrnBT14 ΔlacZWJ16 hsdR514 ΔaraBADAH33 ΔrhaBADLD78) derivative with F' transduced from XL-1 blue to supply LacIq and the deletion of adhE, ldhA, frdBC, fnr, pta and pflB. To replace enzyme YqhD in Example 1 by AdhP enzyme, two fragments were generated and joined together using DNA assembly. *E. coli* adhP gene was amplified by PCR using the primers EB938 and EB9-41. Plasmid pYX97 was used as a backbone with the entire plasmid except yqhD being amplified. Primers for the backbone construction of pCL9 from pYX97 were EB9-39 and EB9-40. Plasmid pCL9 was created by DNA assembly using the adhP fragment and the backbone of pYX97. In the presence of isopropyl-β-D-thiogalactoside (IPTG), plasmid pCL9 can overexpress the enzymes LeuDH, KivD and AdhP in host *E. coli* strains.

*E. coli* strain JCL260/pCL9 (JCL260 containing the plasmid pCL9) were pre-cultured in test tubes containing LB medium with a ampicillin at 37° C. overnight on a rotary shaker. Overnight cultures were diluted 1:100 into a different fresh medium. The fresh medium was 1× M9 with 5 g/L BD yeast extract and 100 μg/mL ampicillin 1× modified M9 salt contains 31.5 g/l NaHPO$_4$, 15 g/l KH$_2$PO$_4$, 2.5 g/l NaCl, 120 mg/l MgSO$_4$, 11 mg/L CaCl$_2$, 10 mg/l vitamin B, 0.2 mM isopropyl-β-D-thiogalactoside (IPTG), and 70 g/L L-Valine per liter water. As analyzed by the provider (Becton Dickinson), 5 g/L BD yeast extract contains 2.71 g/l amino acids, 0.56 g/L ash, 0.38 g/l various salts, 0.16 g/L H$_2$O as well as 0.82 g/l carbohydrate, which is nondegradable by *E. coli*. In some samples, 0.2% of glycerol was added. Fermentation was performed at 37° C. on a rotary shaker. After 16 hours of fermentation, the fermentation broths were analyzed by GC, GC-MS and HPLC as described in Example 5 above.

Figure 14:
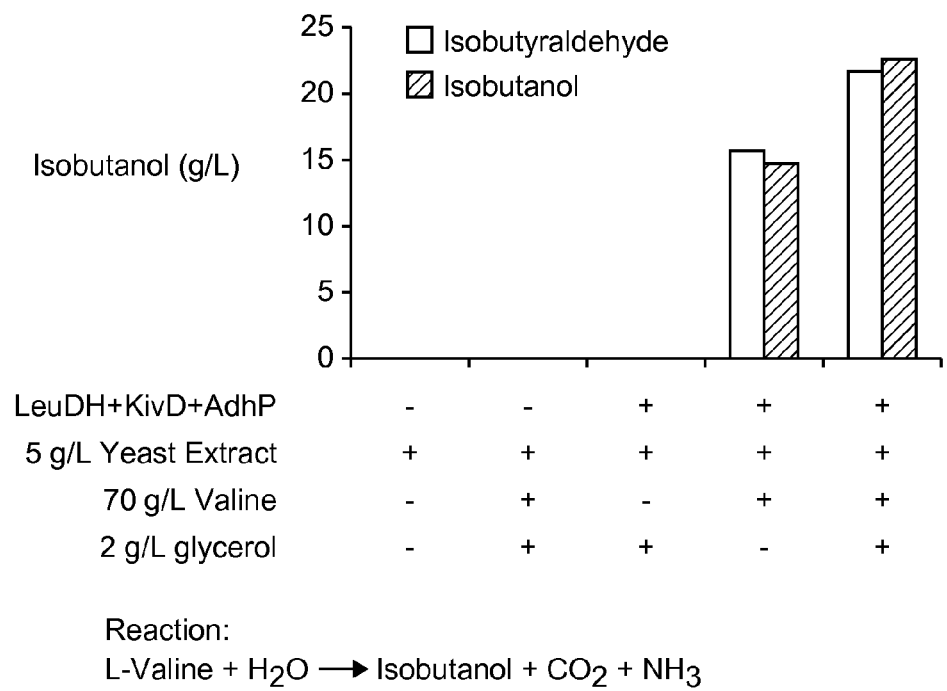
FIG. 14 is a bar graph depicting isobutanol and isobutyraldehyde production (g/L) from valine by an *E. coli* strain containing LeuDH-kivD-adhP genes compared to that of to an *E. coli* strain not containing those genes, in the presence and absence of supplemental valine, yeast extract and glycerol.

Typical results are shown in FIG. 14. No isobutanol was detected in the broth containing JCL260 strain, regardless of whether or not L-valine had been added. In the absence of valine, low concentrations (0.08 g/L) of isobutanol were detected in the broth containing JCL260/pCL9. In this example, the glycerol could not be converted to biofuel by JCL260/pCL9. However, the present of 0.2% glycerol (2 g/L) provide additional reducing power (reduced NADH) to the cell culture and could increase the biofuel titer. In the presence of 70 g/L L-valine a high concentration (22.6 g/L) of isobutanol was detected in the broth containing JCL260/pCL9. In addition to the isobutanol produced, there was 21.8 g/L isobutyraldehyde produced in the same broth. Isobutyraldehyde is a very useful chemical and biofuel, and could be converted to isobutanol by microorganism or chemical conversion. The theoretical conversion rate from L-valine to biofuel (isobutanol or isobutyraldehyde) was 0.63 g/g. These results demonstrate that 44.4 g/L isobutanol and isobutyraldehyde was produced directly from 70 g/L L-valine by the enzymes LeuDH-KivD-YqhD; approximately 100% of the theoretical yield was achieved in this particular study.

Example 7

This example demonstrates 3-methyl-1-butanol production from leucine by an *E. coli* strain containing LeuDH-KivD-YqhD genes.

*E. coli* strain JCL16, and the *E. coli* strain JCL16/pYX97 (JCL16 containing the plasmid pYX97) were pre-cultured in LB medium at 37° C. overnight on a rotary shaker with ampicillin (100 μg/ml) as described in Example 1. Overnight cultures were diluted 1:100 into a different fresh medium (1× M9 with 10 g/L BD yeast extract and 100 μg/ml ampicillin) and grown 2 hours at 37° C. before adding 0.1 mM isopropyl-β-D-thiogalactoside (IPTG). After an additional 2 hours 2.5 g/L L-leucine was added to specific culture flasks. Fermentation was performed at 37° C. on a rotary shaker. After 16 hours of fermentation, the fermentation broths were analyzed by GC, GC-MS as described in Example 5 above.

Figure 15:
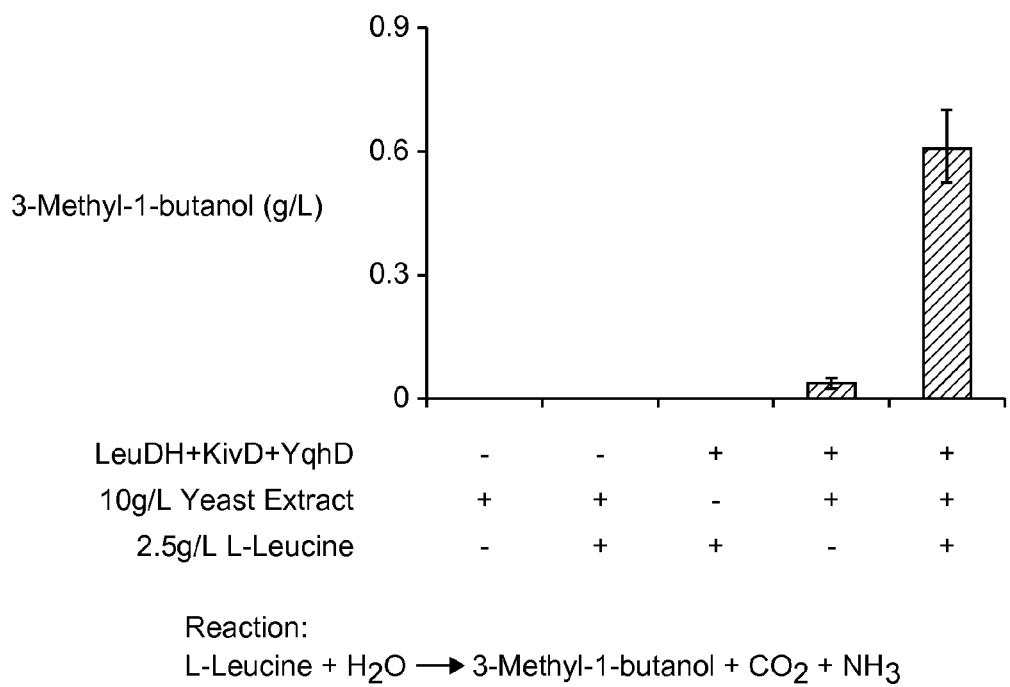
FIG. 15 is a bar graph depicting 3-methyl-1-butanol production (g/L) from leucine by an *E. coli* strain containing LeuDH-kivD-yqhD genes compared to that of an *E. coli* strain not containing those genes, in the presence and absence of supplemental leucine and yeast extract.

Typical results are shown in FIG. 15. No 3-methyl-1-butanol could be detected from the broth containing JCL16 strain in either the presence or absence of L-leucine. In the absence of L-leucine, 0.03 g/L 3-methyl-1-butanol could be detected in the broth containing JCL16/pYX97. In the presence of 2.5 g/L L-leucine, 0.61 g/L 3-methyl-1-butanol could be detected from the broth containing JCL16/pYX97. The theoretical conversion rate from L-leucine to 3-methyl-1-butanol is 0.67 g/g. These results demonstrate that 0.58 g/L of 3-methyl-1-butanol can be produced directly from 2.5 g/L L-leucine by the enzymes LeuDH. Therefore, 35% of the theoretical yield was achieved in this particular study.

Example 8

This example demonstrates 2-methyl-1-butanol production from isoleucine by a strain of *E. coli* containing LeuDH-KivD-YqhD genes.

*E. coli* strain JCL16, and the *E. coli* strain JCL16/pYX97 (JCL16 containing the plasmid pYX97) were pre-cultured LB medium containing ampicillin (100 μg/ml) at 37° C. overnight on a rotary shaker. Overnight cultures were diluted 1:100 into a different fresh medium. The fresh medium was 1× M9 with 10 g/L BD yeast extract and 100 μg/mL ampicillin Cells were grown 2 hours at 37° C. before adding 0.1 mM isopropyl-β-D-thiogalactoside (IPTG). After an additional 2 hours 2.5 g/L L-isoleucine were added to specific culture flasks. Fermentation was performed at 37° C. on a rotary shaker. After 16 hours of fermentation, the fermentation broth was analyzed by GC and GC-MS as described in Example 5 above.

Figure 16:
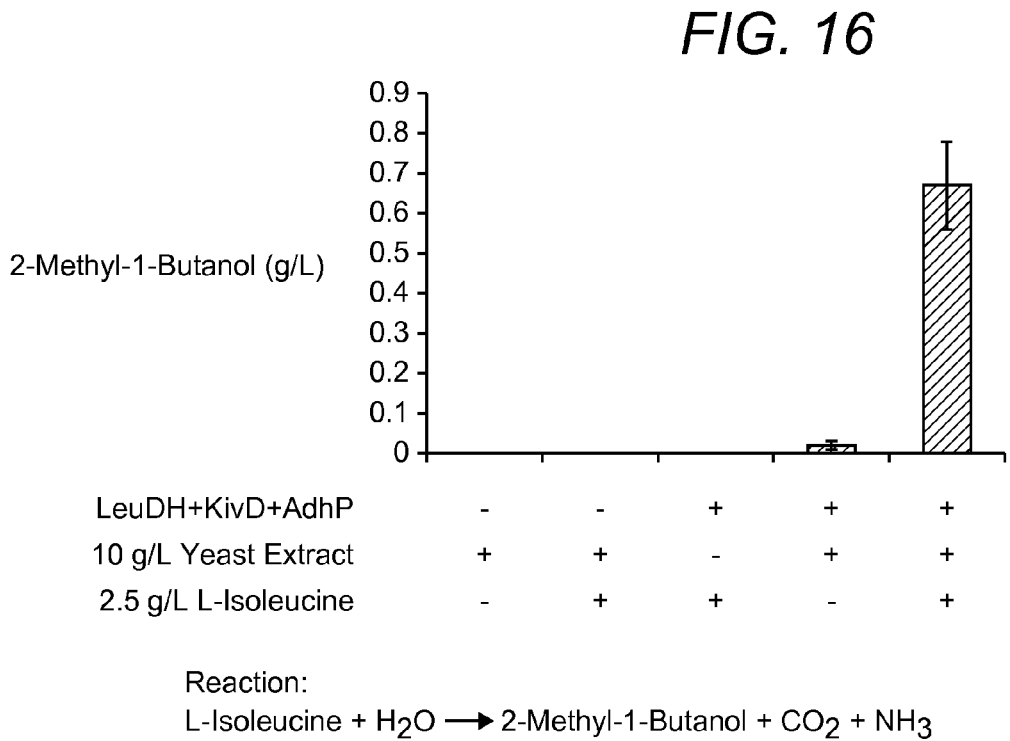
FIG. 16 is a bar graph depicting 2-methyl-1-butanol production (g/L) from isoleucine by an *E. coli* strain containing LeuDH-kivD-yqhD genes compared to that of an *E. coli* strain not containing those genes, in the presence and absence of supplemental isoleucine and yeast extract.

Typical results are shown in FIG. 16. No 2-methyl-1-butanol could be detected from the broth containing JCL16 strain in either the presence or absence of L-isoleucine. In the absence of L-isoleucine, 0.02 g/L 2-methyl-1-butanol could be detected from the broth containing JCL16/pYX97. In the presence of 2.5 g/L L-isoleucine, 0.67 g/L 2-methyl-1-butanol could be detected from the broth containing JCL16/pYX97. The theoretical conversion rate from L-isoleucine to 2-methyl-1-butanol is 0.67 g/g. These results show that 0.65 g/L 2-methyl-1-butanol can be produced directly from 2.5 g/L L-isoleucine by the enzymes LeuDH. Therefore, 39% of the theoretical yield was achieved in this particular study.

Example 9

This example demonstrates conversion from L-valine to 2-ketoisovalerate by *Thermoactinomyces intermedius* LeuDH enzyme using an in vitro enzyme preparation from broken or permeabilized cells (*E. coli* JCL16/pYX51).

To evaluate the direct deamination activity (i.e., production of branched-chain keto acids from branched-chain amino acids) of *Thermoactinomyces intermedius* LeuDH (E.C. number 1.4.1.9, GenBank ID: CAA55671.1), *E. coli* strain JCL16 was transformed with pYX51. To clone pYX51, primers YXH01 and YXH02 were used to amplify *Thermoactinomyces intermedius* leuDH. The PCR product was digested with Acc65I and SalI and cloned into an empty plasmid pYK (a derivative of pSA40) digested with the same enzymes.

*E. coli* JCL16 cells with and without pYX51 were grown at 30° C. in 4% yeast extract media for 12 hours following IPTG induction. LeuDH crude extracts were prepared by concentrating the cultures tenfold in 0.1 M phosphate buffer (pH 7.1) and lysing them with 0.1 mm glass beads. Total protein concentrations were measured by Bradford assays. An *E. coli* strain without gene overexpression was used as a background control.

Figure 17:
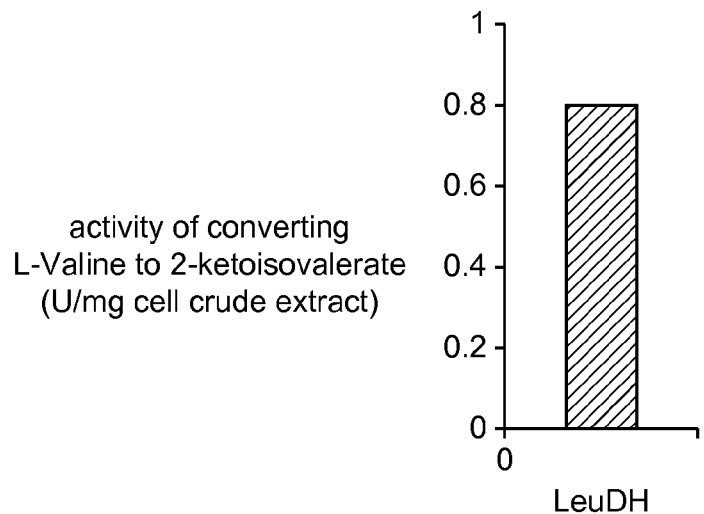
FIG. 17 is a bar graph depicting conversion from L-valine to 2-ketoisovalerate by *Thermoactinomyces intermedius* LeuDH enzyme using an in vitro enzyme process utilizing broken cells (*E. coli* JCL16/pYX51).

Enzyme activity was characterized by mixing 179 mM glycine, 179 mM potassium chloride, 18 mM L-valine, 1.1 mM β-NAD+, and 0.37 mM potassium phosphate with LeuDH crude extract incubating at 37° C. Changes in optical density at 340 nm were recorded over time. 1 U was defined as the activity necessary for the formation of 1 μmol NADH per minute at 37° C. for the oxidative deamination of L-valine. Specific activity was expressed as U/mg protein. Typical results are shown in FIG. 17, and show that the LeuDH activity of direct deamination of L-valine was 0.7 U/mg for LeuDH crude extract in this study.

Example 10

This example demonstrates conversion from L-leucine to 2-ketoisocaproate by *Thermoactinomyces intermedius* LeuDH enzyme using an in vitro enzyme preparation from broken or permeabilized cells (*E. coli* JCL16/pYX51).

Figure 18:
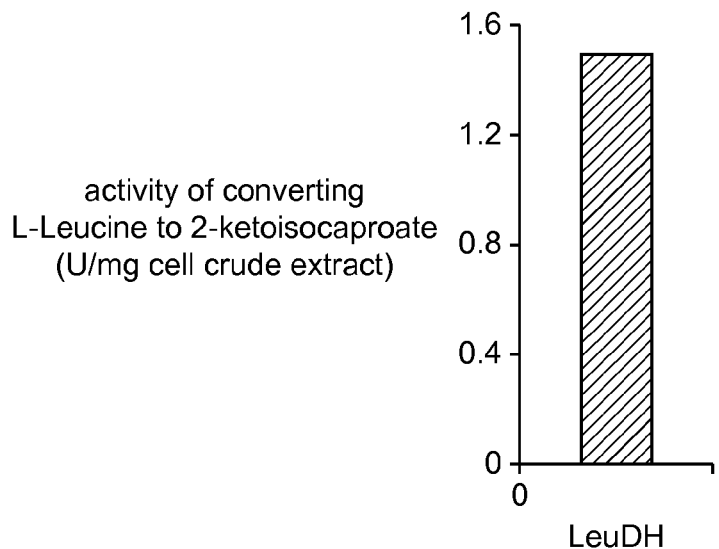
FIG. 18 is a bar graph depicting conversion from L-Leucine to 2-ketoisocaproate by *Thermoactinomyces intermedius* LeuDH enzyme using an in vitro enzyme process utilizing broken cells (*E. coli* JCL16/pYX51).

JCL16 cells were prepared as described in Example 9, with and without pYX51. Crude extracts were also prepared and analyzed as in Example 9. Enzyme activity was measured by mixing samples with 179 mM glycine, 179 mM potassium chloride, 18 mM L-leucine, 1.1 mM β-NAD+, 0.37 mM potassium phosphate and 10 μL LeuDH crude extract and incubating at 37° C. The change in optical density at 340 nm was recorded over time. 1 U was defined as the activity necessary for the formation of 1 μmol NADH per minute at 37° C. in the oxidative deamination of L-leucine. Specific activity was expressed as U/mg protein. Typical results are shown in FIG. 18, and show that the LeuDH activity for direct deamination of L-leucine was 1.5 U/mg for LeuDH crude extract in this study.

Example 11

This example demonstrates conversion from L-isoleucine to 2-keto-3-methyl-valerate by *Thermoactinomyces intermedius* LeuDH enzyme using an in vitro enzyme preparation from broken or permeabilized cells (*E. coli* JCL16/pYX51).

JCL16 cells were prepared as described in Example 9, with and without pYX51. LeuDH crude extracts were also prepared and analyzed as in Example 9.

Enzyme activity was characterized by mixing 179 mM glycine, 179 mM potassium chloride, 18 mM L-isoleucine, 1.1 mM β-NAD+, 0.37 mM potassium phosphate with LeuDH crude extracts and incubating at 37° C. Changes in optical density at 340 nm were recorded over time. 1 U was defined as the activity necessary for the formation of 1 μmol of NADH per minute at 37° C. for the oxidative deamination of L-isoleucine. Specific activity was expressed as U/mg protein. Typical results are shown in FIG. 19, and show that the LeuDH activity for direct deamination of L-isoleucine is 1.9 U/mg for LeuDH crude extract in this study.

Example 12

This example demonstrates the production of Isobutanol from Valine by purified LeuDH, KivD and AdhP proteins (FIG. 20).

LeuDH was purified from a BL21(DE3) strain containing plasmid pEB3-146. KivD was purified from a BL21(DE3) strain containing plasmid pEB3-147. AdhP was purified from a BL21(DE3) strain containing plasmid pEB0202. Proteins were purified individually by incubating the strain overnight in a 5 mL LB tube with appropriate antibiotic at 250 RPM on a rotary shaker at 37° C., the next morning the cell culture from the tube was transferred into a 500 mL flask containing 250 mL LB with the appropriate antibiotic and the flask was placed on a 250 RPM rotary shaker at 37° C. for 2-3 hours, then 0.1M isopropyl-β-D-thiogalactosidase (IPTG) was added. The cell culture was inoculated for another 5-6 hours before it was centrifuged for 30 min at 4° C. at 4000 RPM. The pellet was saved at −20° C. The Pellet was used to make the purified protein using the Ni-NTA kit. The concentration of purified LeuDH protein was 81.6 μM, purified KivD was 19.9 μM, and purified AdhP was 93.6 μM.

The valine to isobutanol conversion was done inside a vial containing 50 g/L valine, 40 g/L pH 8.0 3-(N-morpholino)propanesulfonic acid (MOPS), 0.19 g/L $MgCl_2$, 0.4 g/L Thiamin Pyrophosphate (TPP), 0.0625 mM NAD+, 2 mM NADH, and enzymes LeuDH (16.3 μM), KivD (3.98 μM), and AdhP (18.7 μM). After 4 days, 28.7 g/L of L-Valine was consumed and the concentration of Isobutanol reached 18 g/L, which corresponds to 0.63 g isobutanol/g valine.

Example 13

This example demonstrates the production of n-butanol from L-Norvaline by purified LeuDH, KivD and AdhP proteins (FIG. 21).

LeuDH, KivD and AdhP were purified as described in Example 12.

The leucine to 3-methyl-1-butanol conversion was done inside a vial containing 50 g/L Norvaline, 40 g/L pH 8.0 3-(N-morpholino)propanesulfonic acid (MOPS), 0.19 g/L $MgCl_2$, 0.4 g/L Thiamin Pyrophosphate (TPP), 0.5 mM NAD+, 2 mM NADH, and enzymes LeuDH (16.3 μM), KivD (3.98 μM), and AdhP (18.7 μM). After 2 hours, the concentration of norvaline reached 2.9 mg/L. The concentration of consumed Norvaline is too low to be quantitatively measured by HPLC.

Example 14

This example demonstrates the production of 3-methyl-1-butanol from Leucine by purified LeuDH, KivD and AdhP proteins (FIG. 22).

LeuDH, KivD and AdhP were purified as described in Example 12.

The leucine to 3-methyl-1-butanol conversion was done inside a vial containing 50 g/L leucine, 40 g/L pH 8.0 3-(N-morpholino)propanesulfonic acid (MOPS), 0.19 g/L MgCl$_2$, 0.4 g/L Thiamin Pyrophosphate (TPP), 0.5 mM NAD+, 2 mM NADH, and enzymes LeuDH (16.3 μM), KivD (3.98 μM), and AdhP (18.7 μM). After 4 days, 6.7 g/L Leucine was consumed and the concentration of 3-methyl-1-butanol reached 4.1 g/L, which corresponds to 0.61 g 3-methyl-1-butanol/g Leucine.

Example 15

This example demonstrates the production of 2-methyl-1-butanol from Isoleucine by purified LeuDH, KivD and AdhP proteins (FIG. 23).

LeuDH, KivD and AdhP were purified as described in Example 12.

The concentration of LeuDH protein is 81.6 μM, KivD is 19.9 μM, and AdhP is 93.6 μM. The isoleucine to 2-methyl-1-butanol conversion was done inside a vial containing 50 g/L Isoleucine, 40 g/L pH 8.0 3-(N-morpholino)propanesulfonic acid (MOPS), 0.19 g/L MgCl$_2$, 0.4 g/L Thiamin Pyrophosphate (TPP), 0.5 mM NAD+, 2 mM NADH, and enzymes LeuDH (16.3 μM), KivD (3.98 μM), and AdhP (18.7 μM). After 4 days, 10.7 g/L of Isoleucine was consumed and the concentration of 2-methyl-1-butanol reached 6.9 g/L, which corresponds to 0.64 g 2-methyl-1-butanol/g Isoleucine.

Example 16

This example demonstrates the in vitro production of isobutanol from L-lactate by purified enzymes.

Isobutanol is converted from Lactate by purified Ldh, AlsS, IlvC, IlvD, KivD, AdhP, and yqhD proteins. *Lactococcus Lactis* Ldh was purified from a BL21(DE3) strain containing plasmid pEB3-162. AlsS was purified from a BL21(DE3) strain containing plasmid pSA-159. IlvC was purified from a BL21(DE3) strain containing plasmid pEB3-148. IlvD was purified from a BL21(DE3) strain containing plasmid pEB3-149. KivD was purified from a BL21(DE3) strain containing plasmid pEB3-147. AdhP was taken from a BL21(DE3) strain containing plasmid pEB0202. YqhD was purified from a BL21(DE3) strain plasmid containing pEB0180. Proteins were purified individually by incubating the host strain overnight in a 5 mL LB tube with appropriate antibiotic at 250 RPM on a rotary shaker at 37° C. The next morning the cell culture from the tube is transferred into a 500 mL flask containing 250 mL LB with the appropriate antibiotic and the flask was placed on a 250 RPM rotary shaker at 37° C. for 2-3 hours, then 0.1M isopropyl-β-D-thiogalactosidase (IPTG) is added. The cell culture was inoculated for another 5-6 hours before it was centrifuged for 30 min at 4° C. at 4000 RPM. The pellet was saved at −20° C. The Pellet was used to make the purified protein using the Ni-NTA kit. The concentration of purified LDH protein was 3.92 μM, purified AlsS was 22.4 μM, purified IlvC was 175 μM, purified IlvD was 46.1 μM, purified KivD was 19.9 μM, purified AdhP was 93.6 μM, and purified yqhD was 178.8 μM.

The Lactate to isobutanol conversion was done inside a vial containing 0.1M Sodium L-Lactate, 40 g/L pH 8.0 3-(N-morpholino)propanesulfonic acid (MOPS), 0.19 g/L MgCl$_2$, 0.4 g/L Thiamin Pyrophosphate (TPP), 0.5 mM NAD+, 2 mM NADH, and enzymes LDH (196 nM), AlsS (448 nM), IlvC (3.5 μM), IlvD (922 nM), KivD (398 nM), AdhP (1.87 μM), and YqhD (3.57 μM). After 2 hours, the concentration of Isobutanol was not high enough to be quantitatively measured.

Example 17

FIG. 24 shows the effect of different alcohol dehydrogenases on the L-Valine to isobutanol conversion.

Isobutanol is converted from Valine by purified LeuDH, KivD and one alcohol dehydrogenase (AdhA, YqhD or AdhP) as summarized in FIG. 24B. LeuDH was purified from a BL21(DE3) strain containing plasmid pEB3-146. KivD was purified from a BL21(DE3) strain containing plasmid pEB3-147. AdhP was taken from a BL21(DE3) strain containing plasmid pEB0202. YqhD was purified from a BL21(DE3) strain plasmid containing pEB0180. AdhA was purified from a BL21(DE3) strain plasmid containing pEB3-150. Proteins were purified individually by incubating the host strain overnight in a 5 mL LB tube with appropriate antibiotic at 250 RPM on a rotary shaker at 37° C. The next morning the cell culture from the tube is transferred into a 500 mL flask containing 250 mL LB with the appropriate antibiotic and the flask was placed on a 250 RPM rotary shaker at 37° C. for 2-3 hours, then 0.1M isopropyl-β-D-thiogalactosidase (IPTG) is added. The cell culture was inoculated for another 5-6 hours before it was centrifuged for 30 min at 4° C. at 4000 RPM. The pellet was saved at −20° C. The Pellet was used to make the purified protein using the Ni-NTA kit. The concentration of purified LeuDH protein was 81.6 μM, purified KivD was 19.9 μM, purified AdhP was 93.6 μM, purified AdhA was 14.9 μM, and purified yqhD was 178.8 μM. The final concentration of each alcohol dehydrogenase was adjusted to be the same (3 μM) in each reaction and the enzyme assay was done as described in Example 12.

Fermentative isobutanol production from Valine was summarized as in FIG. 24C. LeuDH, KivD and one of the alcohol dehydrogenase (AdhA, YqhD or AdhP) were overexpressed in the host. The fermentation was done as described in Example 6.

Surprisingly, it was found that the alcohol dehydrogenase/acetaldehyde reductase enzyme that is a product of the AdhP gene is particularly useful in the production of branched chain alcohols, such as isobutanol. This enzyme utilizes the cofactor NADH. The reduced NADH produced from the Valine deamination could be used directly by AdhP to convert isobutyraldehyde into isobutanol. The final isobutanol concentration in the presence of AdhP, LeuDH and KivD is 18 g/L in the in vitro enzyme assay and is 22.6 g/L in fermentor.

Example 18

Typical yields from methods and systems of the inventive concept are summarized below in Table 2. Some concentrations could not be quantitatively measured and the corresponding values are marked as ND. ND, not determined.

TABLE 2

| Alcohol Product Pathway | Concentration (g/L) | Productivity (g/(L hour)) | Yield (g/g) |
|---|---|---|---|
| valine to isobutanol | 18 | 3.1 | 0.63 |
| Norvaline to n-butanol | 0.0029 | 0.002 | ND |
| leucine to 3-methyl-1-butanol | 4.1 | 0.2 | 0.64 |
| isoleucine to 2-methyl-1-butanol | 6.9 | 0.2 | 0.64 |
| lactic acid to isobutanol | | ND | |
| lactic acid to ethanol | | ND | |

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for producing branched chain or higher alcohols comprising:
   providing a first bioreactor comprising a first biological catalyst system wherein the first bioreactor converts a feedstock comprising a carbon source into an amino acid product;
   providing a second bioreactor comprising a second biological catalyst system;
   wherein the amino acid product of the first bioreactor is introduced into the second bioreactor, and at least a portion of the amino acid product is converted in the second bioreactor into a branched chain or higher alcohol and a nitrogen byproduct,
   wherein the first biological catalyst system is not capable of producing the branched chain or higher alcohol,
   wherein the first biological catalyst system comprises at least one enzyme selected from the group consisting of leucine dehydrogenase (LeuDH, EC No. 1.4.1.9), threonine amino-lyase (ilvA, EC No. 4.3.1.19), acetohydroxy acid isomeroreductase (ilvC, EC No. 1.1.1.86), dihydroxy acid dehydratase (ilvD, No. 4.2.1.9), L-threonine dehydrase (tdcB, EC No. 4.3.1.17), acetolactate synthase (AlsS, EC No. 2.2.1.6), isopropylmalate synthase (LeuA, EC No. 2.3.3.13), isopropylmalate dehydrogenase (LeuB, EC No. 1.1.1.85), lactate dehydrogenase (LdhA, EC No. 1.1.1.27), EC No. 2.6.1.42, and EC number 4.2.1.33; and
   wherein the second biological catalyst system comprises at least one enzyme selected from the group consisting of leucine dehydrogenase (LeuDH, EC No. 1.4.1.9), alcohol dehydrogenase (NADP+) (YqhD, EC No. 1.1.1.2), alcohol dehydrogenase (AdhP, EC No. 1.1.1.1), lactate dehydrogenase (Ldh, EC No. 1.1.1.27), acetolactate synthase (AlsS, EC No. 2.2.1.6), acetohydroxy acid isomeroreductase (ilvC, No. 1.1.1.86), dihydroxy acid dehydratase (ilvD, No. 4.2.1.9), lactate dehydrogenase (LdhA, EC No. 1.1.1.27), E.C. number 1.1.1.265, E.C. number 1.4.1.2, E.C. number 1.4.1.3, E.C. number 1.4.1.4, E.C. number 1.4.1.8, E.C. number 1.4.1.20, E.C. number 4.1.1.72, E.C. number 4.1.1.74, E.C. number 4.3.1.1, E.C. number 4.3.1.17, E.C. number 4.3.1.18, E.C. number 4.3.1.19, E.C. number 4.3.1.23, E.C. number 4.3.1.24, and E.C. number 4.3.1.25.

2. The method of claim 1, wherein the first bioreactor further converts the carbon source of the feedstock into an organic acid.

3. The method of claim 2, wherein the organic acid is lactic acid.

4. The method of claim 1, wherein the branched chain or higher alcohol is selected from the group consisting of isobutanol, butanol, and 2-butanol.

5. The method of claim 1, wherein the first biological catalyst system comprises a plurality of cells.

6. The method of claim 5, wherein at least one of the plurality of cells originates from an organism that belongs to a genus selected from the group consisting of *Clostridium*, *Zymonomas*, *Escherichia*, *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, *Pichia*, *Candida*, *Hansenula*, *Synechococcus*, *Synechocystis*, *Anabaena*, *Ralstonia*, *Lactococcus*, and *Saccharomyces*.

7. The method of claim 1, wherein the second biological catalyst system comprises a plurality of cells.

8. The method of claim 7, wherein at least one of the plurality of cells originates from an organism that belongs to a genus selected from the group consisting of *Clostridium*, *Zymonomas*, *Escherichia*, *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, *Pichia*, *Candida*, *Hansenula*, *Synechococcus*, *Synechocystis*, *Anabaena*, *Ralstonia*, *Lactococcus*, and *Saccharomyces*.

9. The method of claim 1, wherein the first biological catalyst system, the second biological catalyst system, or both biological catalyst systems, comprise a crude enzyme preparation, a purified enzyme preparation, or a recombinant enzyme.

10. The method of claim 1, wherein the first biological catalyst system, the second biological catalyst system, or both biological catalyst systems comprise a substantially cell free extract.

11. The method of claim 1, wherein the first biological catalyst system, the second biological catalyst system, or both biological catalyst systems comprise a plurality of broken or permeabilized cells.

12. The method of claim 1, wherein the first feedstock is a gaseous carbon source.

13. The method of claim 1, wherein the enzyme in the second biological catalyst system is alcohol dehydrogenase encoded by an adhP gene from *Escherichia coli*.

14. The method of claim 1, wherein the amino acid is a branched amino acid.

15. The method of claim 1, wherein the intermediate product is transferred into the second bioreactor.

16. The method of claim 1, wherein, of the carbon comprising the alcohol produced in the second bioreactor, at least about 70% originates from the feedstock comprising a carbon source utilized in the first bioreactor.

17. The method of claim 1, wherein, of the carbon comprising the alcohol produced in the second bioreactor, at least about 90% originates from the feedstock utilized in the first bioreactor.

18. The method of claim 1, wherein the carbon source is 2-ketoisovalerate and the amino acid product is L-valine.

19. The method of claim 1, wherein the carbon source is 2-ketoisocaproate and the amino acid product is L-leucine.

20. The method of claim 1, wherein the carbon source is 2-keto-3-methyl-valerate and the amino acid product is L-isoleucine.

21. The method of claim 1, wherein the carbon source is glucose and the amino acid product is L-valine.

22. The method of claim 1, wherein the amino acid product is L-valine and the alcohol is isobutanol.

23. The method of claim 1, wherein the amino acid product is leucine and the alcohol is 3-methyl-1-butanol.

24. The method of claim 1, wherein the amino acid product is isoleucine and the alcohol is 2-methyl-1-butanol.

25. The method of claim 1, wherein the carbon source is 2-ketoisocaproate and the amino acid product is L-leucine.

26. The method of claim 1, wherein the carbon source is 2-keto-3-methyl-valerate and the amino acid product is L-isoleucine.

27. The method of claim 1, wherein the amino acid product is L-norvaline and the alcohol is n-butanol.

28. The method of claim 1, wherein the amino acid product is leucine and the alcohol is 3-methyl-1-butanol.

29. The method of claim 1, wherein the amino acid product is isoleucine and the alcohol is 2-methyl-1-butanol.

30. The method of claim 22, wherein the isobutanol concentration is at least 18 g/L.

* * * * *